United States Patent
Ben-Gal et al.

(10) Patent No.: US 7,424,409 B2
(45) Date of Patent: *Sep. 9, 2008

(54) STOCHASTIC MODELING OF TIME DISTRIBUTED SEQUENCES

(75) Inventors: Irad Ben-Gal, Ramat Hasharon (IL); Armin Shmilovici, Tel Aviv (IL); Gail Morag, Herzliya (IL); Gonen Zinger, Hadera (IL)

(73) Assignee: Context-Based 4 Casting (C-B4) Ltd., Herzlia (IL)

( * ) Notice: Subject to any disclaimer, the term of this patent is extended or adjusted under 35 U.S.C. 154(b) by 895 days.

This patent is subject to a terminal disclaimer.

(21) Appl. No.: 10/076,620

(22) Filed: Feb. 19, 2002

(65) Prior Publication Data

US 2003/0061015 A1 Mar. 27, 2003

Related U.S. Application Data

(60) Provisional application No. 60/269,344, filed on Feb. 20, 2001.

(51) Int. Cl.
| | |
|---|---|
| *G06F 7/60* | (2006.01) |
| *G06F 17/10* | (2006.01) |
| *G06G 7/48* | (2006.01) |
| *G06K 9/36* | (2006.01) |
| *G06Q 40/00* | (2006.01) |

(52) U.S. Cl. ............ 703/2; 703/6; 703/7; 703/10; 341/107; 341/109; 382/232; 705/35; 705/37

(58) Field of Classification Search ........... 703/2, 703/6–7, 10; 341/107, 109; 382/232; 200/236–240; 705/35, 37

See application file for complete search history.

(56) References Cited

U.S. PATENT DOCUMENTS

| | | | |
|---|---|---|---|
| 4,719,571 A | | 1/1988 | Rissanen et al. |
| 5,640,159 A | * | 6/1997 | Furlan et al. ............ 341/51 |
| 5,763,159 A | | 6/1998 | Simmonds et al. |

(Continued)

FOREIGN PATENT DOCUMENTS

WO WO 02/067075 8/2002

OTHER PUBLICATIONS

Weinberger, M.J., Rissanen J.J., et al. "A Universal Finite Memory Source." IEEE Transactions on Information Theory. May 1995. vol. 41, Issue 3, pp. 643-652.*

(Continued)

*Primary Examiner*—Paul Rodriguez
*Assistant Examiner*—Ayal Sharon

(57) ABSTRACT

Apparatus for building a stochastic model of a time sequential data sequence, the data sequence comprising symbols selected from a finite symbol set, the apparatus comprising: an input for receiving said data sequence, a tree builder for expressing said symbols as a series of counters within nodes, each node having a counter for each symbol, each node having a position within said tree, said position expressing a symbol sequence and each counter indicating a number of its corresponding symbol which follows a symbol sequence of its respective node, and a tree reducer for reducing said tree to an irreducible set of conditional probabilities of relationships between symbols in said input data sequence. The tree may then be used to carry out a comparison with a new data sequence to determine a statistical distance between the old and the new data sequence.

58 Claims, 17 Drawing Sheets

U.S. PATENT DOCUMENTS

| | | | | |
|---|---|---|---|---|
| 5,903,676 | A | * | 5/1999 | Wu et al. .................... 382/244 |
| 5,907,637 | A | * | 5/1999 | Murashita et al. ........... 382/239 |
| 5,986,591 | A | * | 11/1999 | Willems et al. ............... 341/79 |
| 6,542,640 | B1 | * | 4/2003 | Morihara et al. ............ 382/229 |
| 6,801,141 | B2 | * | 10/2004 | Yang et al. ..................... 341/51 |
| 2004/0068332 | A1 | | 4/2004 | Ben-Gal et al. |

OTHER PUBLICATIONS

Weisstein, E.W. "Relative Entropy." From Mathworld—A Wolfram Web Resource. http://mathworld.wolfram.com/RelativeEntropy.html. Printed Dec. 9, 2005.*

Naranjo, S.E. et al. "Resampling Software for Analysis and Validation of Enumerative and Binomal Sampling Plans." Undated. Printed Dec. 9, 2005. http://www.wcrl.ars.usda.gov/software/rvspman.html.*

Rissanen, J. "A Universal Data Compression System." IEEE Transactions on Information Theory. Sep. 1983. vol. 29, Issue 5, pp. 656-664.*

Qian, H. "Relative Entropy: Free Energy Associated with Equilibrium Fluctuations and Non-Equilibrium Deviations." Physical Review E., 2001. vol. 63, pp. 042103/1-042103/4. http://arxiv.org/abs/math-ph/007010.*

Weinberger, M. et al. "Sequential Model Estimation for Universal Coding and the Predictive Stochastic Complexity of Finite-State Sources." Proc. IEEE Int'l Symposium on Info. Theory. Jan. 17-22, 1993, p. 52.*

"Advanced Summer Institute 2000: The Annual Conference of the ICIMS-NOE (E.P. 23447)". Printed Aug. 23, 2006. http://www.lar.ee.upatras.gr/icims/asi/asi2000/asi2000.htm.*

Ben-Gal et al. "Design of Control and Monitoring Rules for State Dependent Processes", Int. J. Manufacturing Science & Prod., Invited Paper, 3(2-4): 85-93, 2000.

Ben-Gal et al. "Context-Based Statistical Process Control: A Monitoring Procedure for State-Dependent Processes", Technometrics, 45(4): 293-311, 2003.

Ben-Gal et al. "Statistical Process Control Via Context Modelling of Finite-State Processes: An Application to Production Monitoring", IIE Transactions, 36: 401-415, 2004.

Shmilovici et al. "Context Dependent ARMA Modeling", 21st IEEE Convention, Tel-Aviv: 249-252, 2000.

Ben-Gal et al. "An Information Theoretic Approach for Adaptive Monitoring of Processes", AS12000, The Annual Conference of ICIMS—NOE and IIMB, Bordeaux, 4 P., 2000.

Zhang et al. "Design of Nanostructured Biological Materials Through Self-Assembly of Peptides and Proteins", Current Opinion in Chemical Biology, 6: 865-871, 2002. not to be IDS'd as per Hadassa (not relevant) May 4, 2006.

Morag G., Ben-Gal I., "Design of Control Charts Based on Context Universal Model", *Proc. of the Industrial Engineering and Management Conference*, Beer-Sheva, May 3-4, 2000, pp. 200-204.

Zinger G., Ben-Gal I., "An Information Theoretic Approach to Statistical Process Control of Autocorrelated Data", Proc. of the Industrial Engineering and Management Conference, Beer-Sheva, May 3-4, 2000, pp. 194-199 (In Hebrew).

Ben-Gal I., Shmilovici A. Morag G., "Design of Control and Monitoring Rules for State Dependent Processes", *The International Journal for Manufacturing Science and Production*, vol. 3, 2-4, 2000, pp. 85-93.

Ben-Gal I., Shmilovici A., Morag G., "Statistical Control of Production Processes via Monitoring of Buffer Levels", *Proc. of the 9$^{th}$ International Conference on Productivity & Quality Research*, Jerusalem, Israel, Jun. 25-28, 2000, pp. 340-347.

Shmilovici A., Ben-Gal I., "Statistical Process Control for a Context Dependent Process Model", *Proc. of the Annual EURO Operations Research Conference*, Budapest, Hungary, Jul. 16-19, 2000, 2 pages.

Singer G. and Ben-Gal I., "A Methodology for Integrating Engineering Process Control and Statistical Process Control", *Proc. of The 16$^{th}$ International Conference on Production Research*, Prague, Czech Republic. Jul. 29-Aug. 3, 2001, 2 pages.

Ben-Gal I., Shmilovici A., "Identifying Promoters by VOM Modeling", Artificial Intelligence and Heuristic Methods for Bioinformatics, Sep. 30-Oct. 12, San-Miniato, Italy, 2001.

* cited by examiner

Fig. 1 SPC Characterization methods

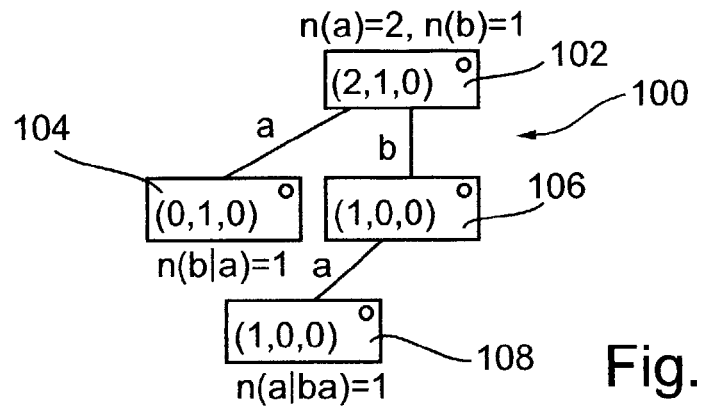
The counter context tree constructed from $x_3$=a,b,a
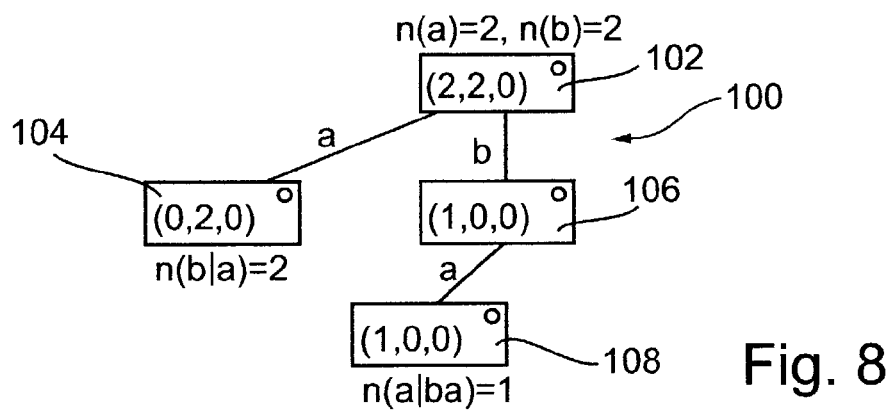
The counter context tree constructed from $x^4$=a,b,a,b following step 1.1
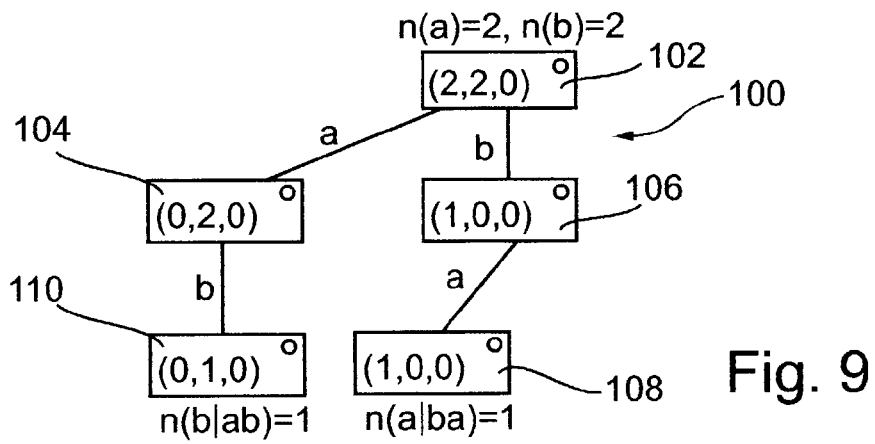
The counter context tree constructed from $x^4$=a,b,a,b; partial application of step 1.2

The pruned counter context-tree of the string
(a,b,a,b,c,a,b,a,b,c,a,b,a,b,a,b,c) replicated 8 times The context tree containing vectors of conditional probabilities P(x|s) as obtained from the counter context-tree in figure A4. Optimal contexts are represented by the bolded frame

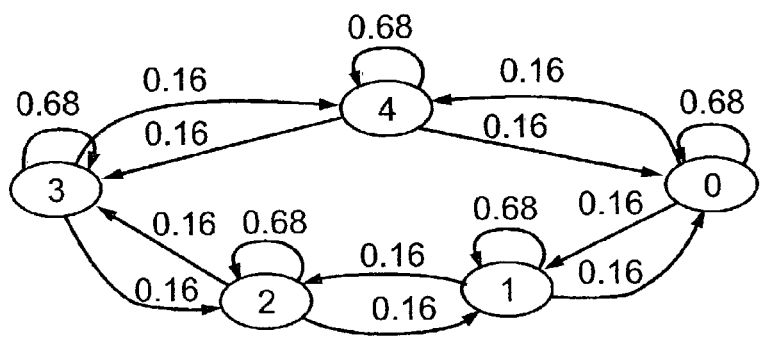
Fig. 12 State transition diagram
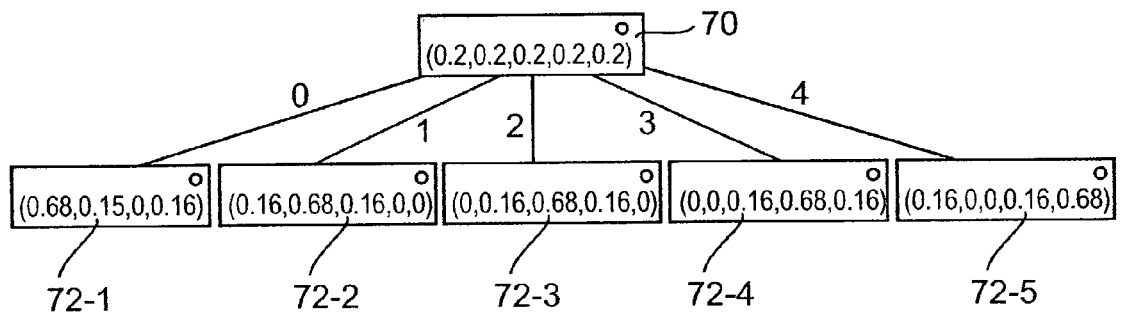
Fig. 13 The analytically derived singled-level context-tree
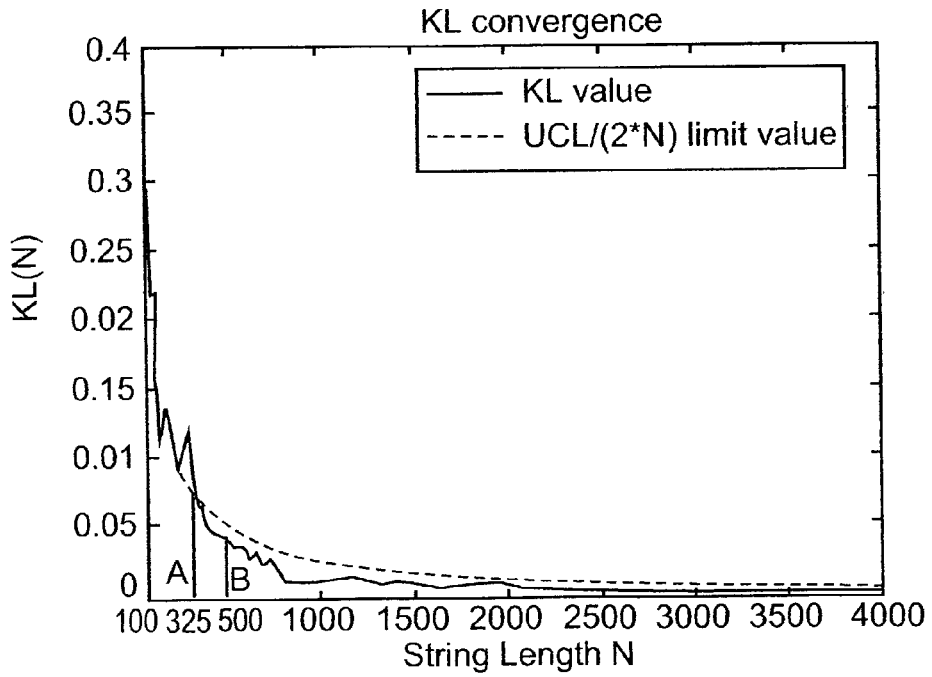
Fig. 14 KL value in relation to input string length N

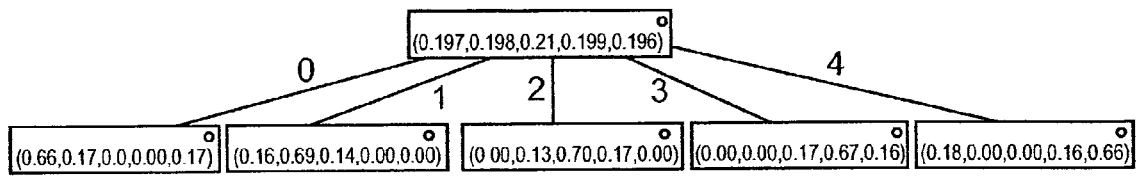
Fig. 15 Estimated reference context-tree resulted from the implementation of context algorithm to N=1000
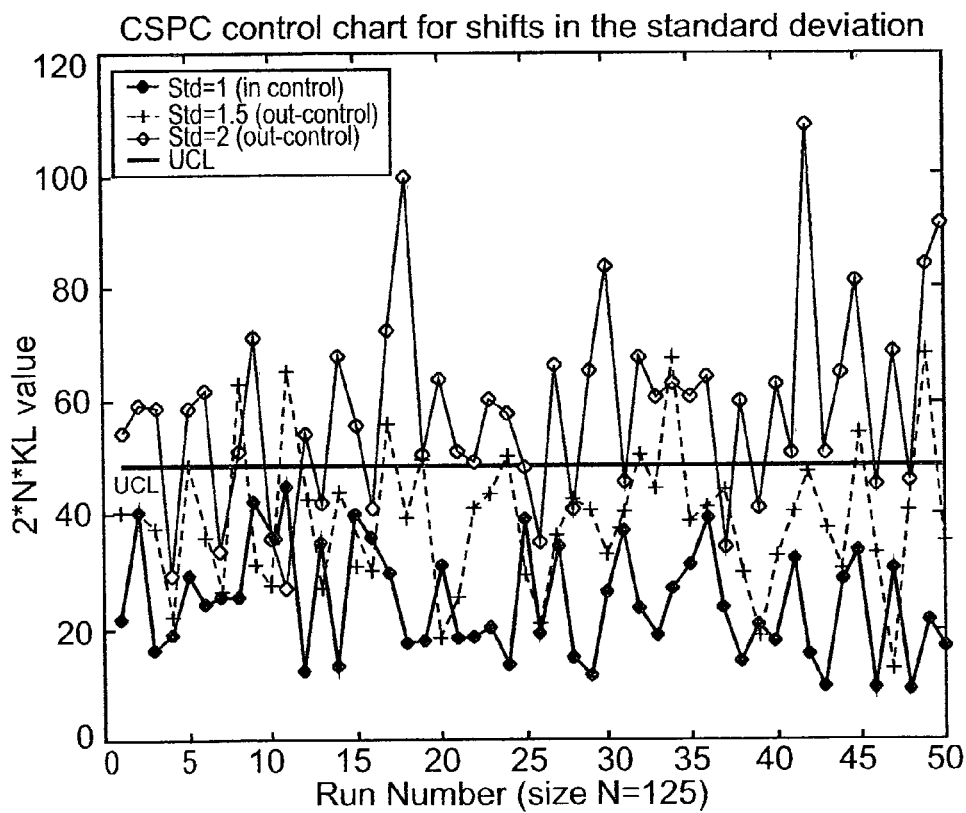
Fig. 16
Shifts in the process underlying normal standard deviation
λ=1,1.5,2 (number of runs for each process properties is equal to 50)

Shift in the process underlying normal standard deviation
λ=0.5 (number of runs equal to 50)

Operating characteristics curve

The SCC control chart for "in-control" data

Shewhart SPC $\overline{X}$ chart-"in-control" data (solid line) and "out-of-control" data (dashed line)

Shewhart SPC *S* chart-"in-control" data (solid line) and "out-of-control" data (dashed line)

Shewhart SPC $\overline{X}$ chart for N=125 sample size - "in-control" data (solid line) and "out-of-control" data (dashed line)

Shewhart SPC S chart for N=125 sample -"in-control" data (solid line) and "out-of-control" data (dashed line)

STOCHASTIC MODELING OF TIME DISTRIBUTED SEQUENCES

RELATIONSHIP TO EXISTING APPLICATIONS

The present application claims priority from U.S. Provisional Patent Application No. 60/269,344 filed Feb. 20, 2001, the contents of which are hereby incorporated by reference.

FIELD OF THE INVENTION

The present invention relates to stochastic modeling of time distributed sequences and more particularly but not exclusively to modeling of data sequences using stochastic techniques, and again but not exclusively for using the resultant models for analysis of the sequence.

BACKGROUND OF THE INVENTION

Data sequences often contain redundancy, context dependency and state dependency. Often the relationships within the data are complex, non-linear and unknown, and the application of existing control and processing algorithms to such data sequences does not generally lead to useful results.

Statistical Process Control (SPC) essentially began with the Shewhart chart and since then extensive research has been performed to adapt the chart to various industrial settings. Early SPC methods were based on two critical assumptions:

i) there exists a priory knowledge of the underlying data distribution (often, observations are assumed to be normally distributed); and ii) the observations are independent and identically distributed (i.i.d.).

In practice, the above assumptions are frequently violated in many industrial processes.

Current SPC methods can be categorized into groups using two different criteria as follows:

1) methods for independent data where observations are not interrelated versus methods for dependent data;

2) methods that are model-specific, requiring a priori assumptions on the process characteristics and its underlying distribution, and methods that are model-generic. The latter methods try to estimate the underlying model with minimum a priori assumptions.

FIG. 1 is a chart of relationships between different SPC methods and includes the following:

Information Theoretic Process Control (ITPC) is an independent-data based and model-generic SPC method proposed by Alwan, Ebrahimi and Soofi (1998). It utilizes information theory principles, such as maximum entropy, subject to constraints derived from dynamics of the process. It provides a theoretical justification for the traditional Gaussian assumption and suggests a unified control chart, as opposed to traditional SPC that require separate charts for each moment.

Traditional SPC methods, such as Shewhart, Cumulative Sum (CUSUM) and Exponential Weighted Moving Average (EWMA) are for independent data and are model-specific. It is important to note that these traditional SPC methods are extensively implemented in industry. The independence assumptions on which they rely are frequently violated in practice, especially since automated testing devices increase the sampling frequency and introduce autocorrelation into the data. Moreover, implementation of feedback control devices at the shop floor level tends to create structured dynamics in certain system variables. Applying traditional SPC to such interrelated processes increases the frequency of false alarms and shortens the 'in-control' average run length (ARL) in comparison to uncorrelated, observations. As shown later in this section, these methods can he modified to control autocorrelated data.

The majority of model-specific methods for dependent data are time-series based. The underlying principle of such model-dependent methods is as follows: assuming a time series model family can best capture the autocorrelation process, it is possible to use that model to filter the data, and then apply traditional SPC schemes to the stream of residuals. In particular, the ARIMA (Auto Regressive Integrated Moving Average) family of models is widely applied for the estimation and filtering of process autocorrelation. Under certain assumptions, the residuals of the ARIMA model are independent and approximately normally distributed, to which traditional SPC can be applied. Furthermore, it is commonly conceived that ARIMA models, mostly the simple ones such as AR(1), can effectively describe a wide variety of industry processes.

Model-specific methods for autocorrelated data can be further partitioned into parameter-dependent methods that require explicit estimation of the model parameters, and to parameter-free methods, where the model parameters are only implicitly derived, if at all.

Several parameter-dependent methods have been proposed over the years for autocorrelated data. Alwan and Roberts (1988), proposed the Special Cause Chart (SCC) in which the Shewhart method is applied to the stream of residuals. They showed that the SCC has major advantages over Shewhart with respect to mean shifts. The SCC deficiency lies in the need to explicitly estimate all the ARIMA parameters. Moreover, the method performs poorly for a large positive autocorrelation, since the mean shift tends to stabilize rather quickly to a steady state value, and the shift is poorly manifested on the residuals (see Wardell, Moskowitz and Plante (1994) and Harris and Ross (1991)).

Runger, Willemain and Prabhu (1995) implemented traditional SPC for autocorrelated data using CUSUM methods. Lu and Reynolds (1997, 1999) extended the method by using the EWMA method with a small difference. Their model had a random error added to the ARIMA model. The drawback of these models is in the exigency of an explicit parameter estimation and estimation of their process-dependence features. It was demonstrated in Runger and Willemain (1995) that for certain autocorrelated processes, the use of traditional SPC yields an improved performance in comparison to ARMA-based methods.

The Generalized Likelihood Ratio Test—GLRT—method proposed by Apley and Shi (1999) takes advantage of residuals transient dynamics in the ARIMA model, when a mean shift is introduced. The generalized likelihood ratio may be applied to the filtered residuals. The method may be compared to the Shewhart CUSUM and EWMA methods for autocorrelated data, inferring that the choice of the adequate time-series based SPC method depends strongly on characteristics of the specific process being controlled. Moreover, in Apley and Shi (1999) and in Runger and Willemain (1995) it is emphasized in conclusion that modeling errors of ARIMA parameters have strong impacts on the performance (e.g., the ARL) of parameter-dependent SPC methods for autocorrelated data. If the process can be accurately defined by an ARIMA time series, the parameter independent SPC methods are superior in comparison to non-parametric methods since they allow efficient statistical analysis. If such a definition is not possible, then the effort of estimating the time series parameters becomes impractical. Such a conclusion, amongst other reasons, triggered the development of parameter-free methods to avoid the impractical estimation of time-series parameters.

A parameter-free model was proposed by Montgomery and Mastrangelo (1991) as an approximation procedure based on EWMA. They suggested using the EWMA statistic as a one step ahead prediction value for the IMA(1,1) model. Their underlying assumption was that even if the process is better described by another member of the ARIMA family, the IMA(1,1) model is a good enough approximation. Zhang (1998), however, compared several SPC methods and showed that Montgomery's approximation performed poorly. He proposed employing the EWMA statistic for stationary processes, but adjusted the process variance according to the autocorrelation effects.

Runger and Willemain (1995, 1996) discussed the weighted batch mean (WBM) and die unified batch mean (UBM) methods. The WBM method assigns weights for the observations mean and defines the batch size so that the autocorrelation among batches reduces to zero. In the UBM method the batch size is defined (with unified weights) so that the autocorrelation remains under a certain level.

Runger and Willemain demonstrated that weights estimated from the ARIMA model do not guarantee a performance improvement and that it is beneficial to apply the simpler UBM method. In general, parameter-free methods do not require explicit ARIMA modeling, however, they are all based on the implicit assumption that the time-series model is adequate to describe the process. While this can be true in some industrial environments, such an approach cannot capture more complex and non-linear process dynamics that depend on the state in which the system operates, for example processes that are described by Hidden Markov Models (HMM) (see Elliot, Lalkhdaraggoun and Moore (1995)).

Further information is available from Ben-Gal I., Shmilovici A., Morag G., "Design of Control and Monitoring Rules for State Dependent Processes", *Journal of Manufacturing Science and Production*, 3, NOS. 2-4, 2000, pp. 85-93; also Ben-Gal I., Morag G., Shmilovici A., "Statistical Control of Production Processes via Context Monitoring of Buffer Levels", submitted, (after revision); Ben-Gal I., Singer G., "Integrating Engineering Process Control and Statistical Process Control via Context Modeling", submitted, (after revision); Shmilovici A. Ben-Gal I., "Context Dependent ARMA Modeling", *Proc. of the 21st IEEE Convention*, Tel-Aviv, Israel, Apr. 11-12, 2000, pp. 249-252; Morag G., Ben-Gal I., "Design of Control Charts Based on Context Universal Model", *Proc. of the Industrial Engineering and Management Conference*, Beer-Sheva, May 3-4, 2000, pp. 200-204; Zinger G., Ben-Gal I., "An Information Theoretic Approach to Statistical Process Control of Autocorrelated Data", *Proc. of the Industrial Engineering and Management Conference*, Beer-Sheva, May 3-4, 2000, pp. 194-199 (In Hebrew); Ben-Gal I., Shmilovici A. Morag G., "Design of Control and Monitoring Rules for State Dependent Processes", *Proc. of the 2000 International CIRP Design Seminar*, Haifa, Israel, May 16-18, 2000, pp. 405-410; Ben-Gal I., Shmilovici A., Morag G., "Statistical Control of Production Processes via Monitoring of Buffer Levels", *Proc. of the 9th International Conference on Productivity & Quality Research*, Jerusalem, Israel, Jun. 25-28, 2000, pp. 340-347; Shmilovici A., Ben-Gal I., "Statistical Process Control for a Context Dependent Process Model", *Proc. of the Annual EURO Operations Research conference*, Budapest, Hungary, Jul. 16-19, 2000; Ben-Gal I., Shmilovici A., Morag G., "An Information Theoretic Approach for Adaptive Monitoring of Processes", ASI2000, *Proc. of The Annual Conference of ICIMS-NOE and IIMB*, Bordeaux, France, Sep. 18-20, 2000; Singer G. and Ben-Gal I., "A Methodology for Integrating Engineering Process Control and Statistical Process Control", *Proc of The 16$^{th}$ International Conference on Production Research*, Prague, Czech Republic, 29Jul.-Aug. 3, 2001; and Ben-Gal I., Shmilovici A., "Promoters Recognition by Varying-Length Markov Models", Artificial Intelligence and Heuristic Methods for Bioinformatics, 30 September-12 October, San-Miniato, Italy. The contents of each of the above documents is hereby incorporated by reference.

SUMMARY OF THE INVENTION

In general, the embodiments of the invention provide an algorithm which can analyze strings of consecutive symbols taken from a finite set. The symbols are viewed as observations taken from a stochastic source with unknown characteristics. Without a priori knowledge, the algorithm constructs a probabilistic model that represents the dynamics and interrelation within the data. It then monitors incoming data strings for compatibility with the model that was constructed. Incompatibilities between the probabilistic model and the incoming strings are identified and analyzed to trigger appropriate actions (application dependent).

According to a first aspect of the present invention there is provided an apparatus for building a stochastic model of a data sequence, said data sequence comprising time related symbols selected from a finite symbol set, the apparatus comprising:

an input for receiving said data sequence, a tree builder for expressing said symbols as a series of counters within nodes, each node having a counter for each symbol, each node having a position within said tree, said position expressing a symbol sequence and each counter indicating a number of its corresponding symbol which follows a symbol sequence of its respective node, and a tree reducer for reducing said tree to an irreducible set of conditional probabilities of relationships between symbols in said input data sequence.

Preferably, said tree reducer comprises a tree pruner for removing from said tree any node whose counter values are within a threshold distance of counter values of a preceding node in said tree.

Preferably, said threshold distance and tree construction parameters are user selectable.

Preferably, said user selectable parameters further comprise a tree maximum depth.

Preferably, said tree construction parameters further comprise an algorithm buffer size.

Preferably, said tree construction parameters further comprise values for pruning constants.

Preferably, said tree construction parameters further comprise a length of input sequences.

Preferably, said tree construction parameters further comprise an order of input symbols.

Preferably, said tree reducer further comprises a path remover operable to remove any path within said tree that is a subset of another path within said tree.

Preferably, said sequential data is a string comprising consecutive symbols selected from a finite set.

The apparatus further comprises an input string permutation unit for carrying out permutations and reorganizations of the input string using external information about a process generating said string.

Preferably, said sequential data comprises output data of a manufacturing process.

Preferably, said output data comprises buffer level data. The process may comprise feedback.

Preferably, said sequential data comprises seismological data.

Preferably, said sequential data is an output of a medical sensor sensing bodily functions Preferably, said output comprises visual image data and said medical sensor is a medical imaging device.

Preferably, said sequential data is data indicative of operation of cyclic operating machinery.

According to a second aspect of the present invention, there is provided apparatus for determining statistical consistency in time sequential data, the apparatus comprising:

a sequence input for receiving sequential data, a stochastic modeler for producing at least one stochastic model from at least part of said sequential data, and a comparator for comparing said sequential stochastic model with a prestored model, thereby to determine whether there has been a statistical change in said data.

Preferably, said stochastic modeler comprises:

a tree builder for expressing said symbols as a series of counters within nodes, each node having a counter for each symbol, each node having a position within said tree, said position expressing a symbol sequence and each counter indicating a number of its corresponding symbol which follows a symbol sequence of its respective node, and a tree reducer for reducing said tree to an irreducible set of conditional probabilities of relationships between symbols in said input data sequence.

Preferably, the prestored model is a model constructed using another part of said time-sequential data.

Preferably, the comparator comprises a statistical processor for determining a statistical distance between said stochastic model and said prestored model.

Preferably, the statistical distance is a KL statistic.

Preferably, the statistical distance is a relative complexity measure. Preferably, said statistical distance comprises an SPRT statistic.

Alternatively or additionally, said statistical distance comprises an MDL statistic.

Alternatively or additionally, said statistical distance comprises a Multinomial goodness of fit statistic.

Alternatively or additionally, said statistical distance comprises a Weinberger Statistic.

Preferably, said tree reducer comprising a tree pruner for removing from said tree any node whose counter values are within a threshold distance of counter values of a preceding node in said tree.

Preferably, said threshold distance is user selectable.

Preferably, user selectable parameters further comprise a tree maximum depth.

Preferably, user selectable parameters further comprise an algorithm buffer size.

Preferably, user selectable parameters further comprise values for pruning constants.

Preferably, user selectable parameters further comprise a length of input sequences.

Preferably, user selectable parameters further comprise an order of input symbols.

Preferably, said tree reducer further comprises a path remover operable to remove any path within said tree that is a subset of another path within said tree.

Preferably, said sequential data is a string comprising consecutive symbols selected from a finite set.

The apparatus preferably comprises an input string permutation unit for carrying out permutations and reorganizations of said sequential data using external information about a process generating said data.

Preferably, said sequential data comprises output data of a manufacturing process, including feedback data.

In an embodiment, said sequential data comprises seismological data.

In an embodiment, said sequential data is an output of a medical sensor sensing bodily functions.

In an embodiment, said sequential data is data indicative of operation of cyclic operating machinery.

Preferably, said data sequence comprises indications of a process state, the apparatus further comprising a process analyzer for using said statistical distance measure as an indication of behavior of said process.

Preferably, said data sequence comprises indications of a process state, the apparatus further comprising a process controller for using said statistical distance measure as an indication of behavior of said process, thereby to control said process.

Preferably, said data sequence comprises multi-input single output data.

Preferably, said data sequence comprises financial behavior patterns.

Preferably, said data sequence comprises time sequential image data sequences said model being usable to determine a statistical distance therebetween.

Preferably, the image data is medical imaging data, said statistical distance being indicative of deviations of said data from an expected norm.

The embodiments are preferably applicable to a database to perform data mining on said database.

According to a third aspect of the present invention there is provided a method of building a stochastic model of a data sequence, said data sequence comprising time related symbols selected from a finite symbol set, the method comprising:

receiving said data sequence, expressing said symbols as a series of counters within nodes, each node having a counter for each symbol, each node having a position within said tree, said position expressing a symbol sequence and each counter indicating a number of its corresponding symbol which follows a symbol sequence of its respective node, and reducing said tree to an irreducible set of conditional probabilities of relationships between symbols in said input data sequence, thereby to model said sequence.

BRIEF DESCRIPTION OF THE DRAWINGS

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 7-11 are simplified diagrams of context trees at various stages of their construction, FIG. 12 is a state diagram of a stochastic process that can be monitored to demonstrate operation of the present embodiments, and FIGS. 13-23 show various stages and graphs in modeling and attempting to control the process of FIG. 12 according to the prior art and according to the present invention.

DESCRIPTION OF THE PREFERRED EMBODIMENTS

Figure 1:
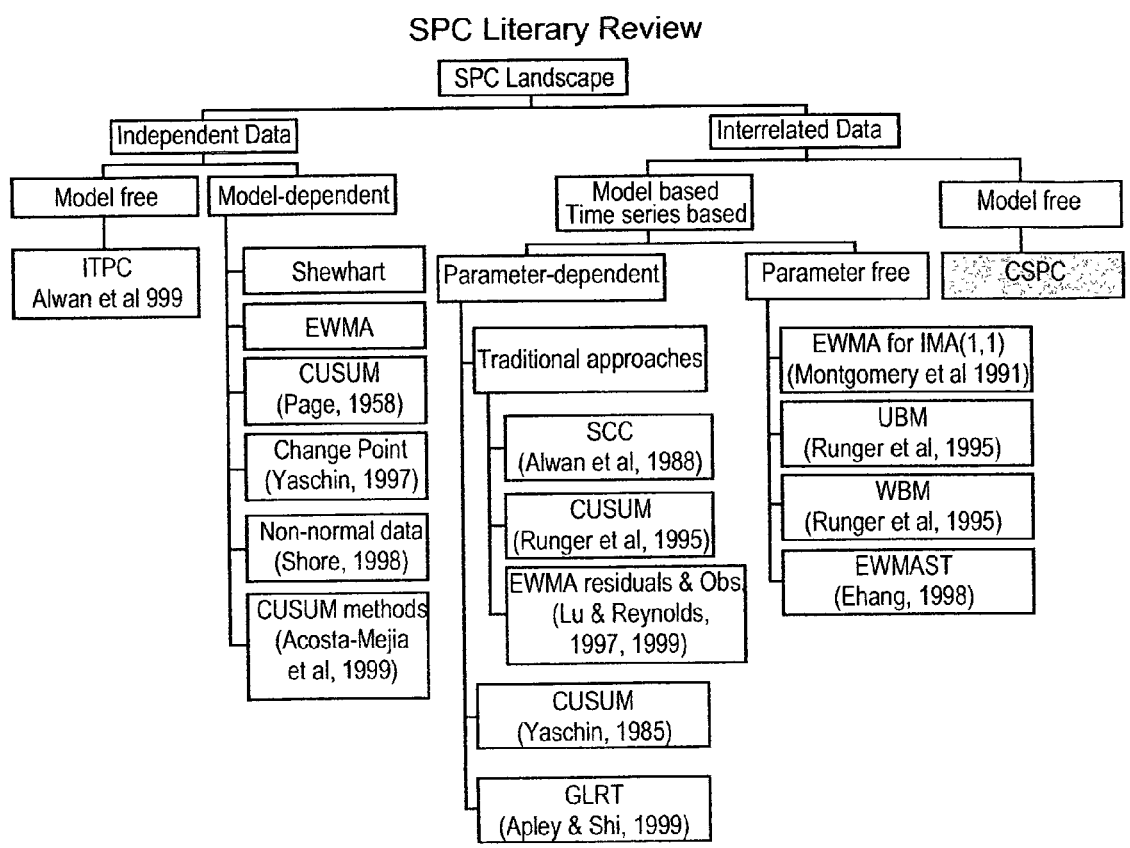
FIG. 1 is a simplified diagram showing the interrelationships between different modeling or characterization methods and specifically showing where the present invention fits in with the prior art.

In the present embodiments, a model-generic SPC method and apparatus are introduced for the control of state-dependent data. The method is based on the context-tree model that was proposed by Rissanen (1983) for data-compression purposes and later for prediction and identification (see Weinberger, Rissanen and Feder (1995)). The context-tree model comprises an irreducible set of conditional probabilities of output symbols given their contexts. It offers a way of constructing a simple and compact model to a sequence of symbols including those describing complex, non-linear processes such as HMM of higher order. An algorithm is used to construct a context tree, and preferably, the algorithm of the context-tree generates a minimal tree, depending on the input parameters of the algorithm, that fits the data gathered.

The present embodiments are based on a modified context-tree that belongs to the above category. The suggested model is different from the models discussed in the background in respect of i) in its construction principles;

ii) its ability to find and compute what we call "partial contexts" and their probabilities—that were found to have vital importance in Biology classification applications; and iii) in the suggested distance measures between different trees. The present embodiments are based on a modified context-tree that belongs to the above category. The suggested model is different from the models discussed in the background in respect of i) in its construction principles;

ii) its ability to find and compute what we call "partial contexts" and their probabilities—that were found to have vital importance in Biology classification applications; and iii) in the suggested distance measures between different trees.

In order to monitor the statistical attributes of a process, the first embodiments compare two context trees at any time during monitoring. For example, in certain types of analysis, it is possible to divide a sequence into subsequences and build trees for each. Thus it is possible to compare several pairs of trees at once with a monitor tree and a reference tree formed from monitor and reference date respectively for each pair. The first context tree is a reference tree that represents the 'in control' referenced behavior of the process, that is to say a model of how the data is expected to behave. The second context tree is a monitored tree, generated periodically from a sample of sequenced observations, which represents the behavior of the process at that period. The first embodiment uses the Kullback-Leibler (KL) statistic (see Kullback (1978)) to measure a relative distance between these two trees and derive an asymptotic distribution of the relative distance. Monitoring the KL estimates with respect to the asymptotic distribution indicates whether there has been any significant change in the process that requires intervention. Again, there are a number of statistics that can be used in addition to or as an alternative to the KL statistic, as will be explained in greater detail below.

As will be explained below, in certain of the embodiments, such as for DNA analysis, a string may be divided into a plurality of substrings for each of which a tree is built. Then several pairs of these trees are compared simultaneously wherein one of the trees in each pair is a reference tree and is generated from a reference or learning data set, and the monitored tree is generated from the monitored data set.

A preferred embodiment of the present invention, hereinafter Context-based SPC (CSPC) has several particular advantages. Firstly, the embodiment learns the dynamics and the underlying distributions within a process being monitored as part of model building. Such learning may be done without requiring a priori information, hence categorizing the embodiment as model-generic. Secondly, the embodiment extends the current limited scope of SPC applications to state-dependent processes including non-linear processes, as will be explained in more detail below. Thirdly, the embodiment provides convenient monitoring of discrete process variables. Finally, the embodiment creates a single control chart for a process to be monitored. The single chart is suited for decomposition if in-depth analysis is required to determine a source of deviation from control limits.

A second embodiment uses the same reference tree to measure the stochastic complexity of the monitored data. Monitoring the analytic distribution of the stochastic complexity, indicates whether there has been any significant change in the process that requires intervention. An advantage of the second embodiment over the first one is that it often requires less monitored data in order to produce satisfactory results.

Other possible statistics that may be used include the following:

Wald's sequential probability ratio testing (SPRT): Wald's test is implemented both in conventional CUSUM and change-point methods and has analytical bounds developed based on the type-I and type-II errors. The advantages of this statistic are that one can detect the exact change point and apply a sequential sample size comparison between the reference and the monitored tree.

MDL (Minimal Description Length): The MDL is the shortest description of a given model and data string by the minimum number of bits needed to encode them.

Such a measure may be used to test whether the reference 'in-control' context-tree and the monitored context-tree are from the same distribution (see Rissanen (1999)).

Multinomial goodness of fit tests: Several goodness of fit tests may be used for multinomial distributions. In general, they can be applied to tree monitoring since any context tree can be represented by a joint multinomial distribution of symbols and contexts. One of the most popular tests is the Kolmogorov-Smirnov (KS) goodness of fit test. Another important test that can be used for CSPC is the Andersen-Darling (AD) test (Law and Kelton (1991)). This test is superior to the KS test for distributions that mainly differ in their tail (i.e., it provides a different weight for the tail).

Weinberger's Statistic: Weinberger et al (1995) proposes a measure to determine whether the context-tree constructed by context algorithm is close enough to the "true" tree model (see eqs. (18), (19)) in their paper). The advantage of such a measure is its similarity to the convergence formula (e.g., one can find bounds for this measure based on the convergence rate and a chosen string length N). However, the measure has been suggested and is more than adequate for coding purposes since it assumes that the entire string N is not available.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Reference is now made to FIG. 1, which is a chart showing characterization of SPC methods and showing how the CSPC embodiments of the present invention relate to existing methods of SPC methods. As discussed above in the background, data sequences can be categorized into independent data and interrelated data, and each of these categories can make use of model specific and model generic methods. The embodiments of the present invention denoted CSPC are characterized as providing a model generic method for interrelated or state dependent data.

Figure 2:
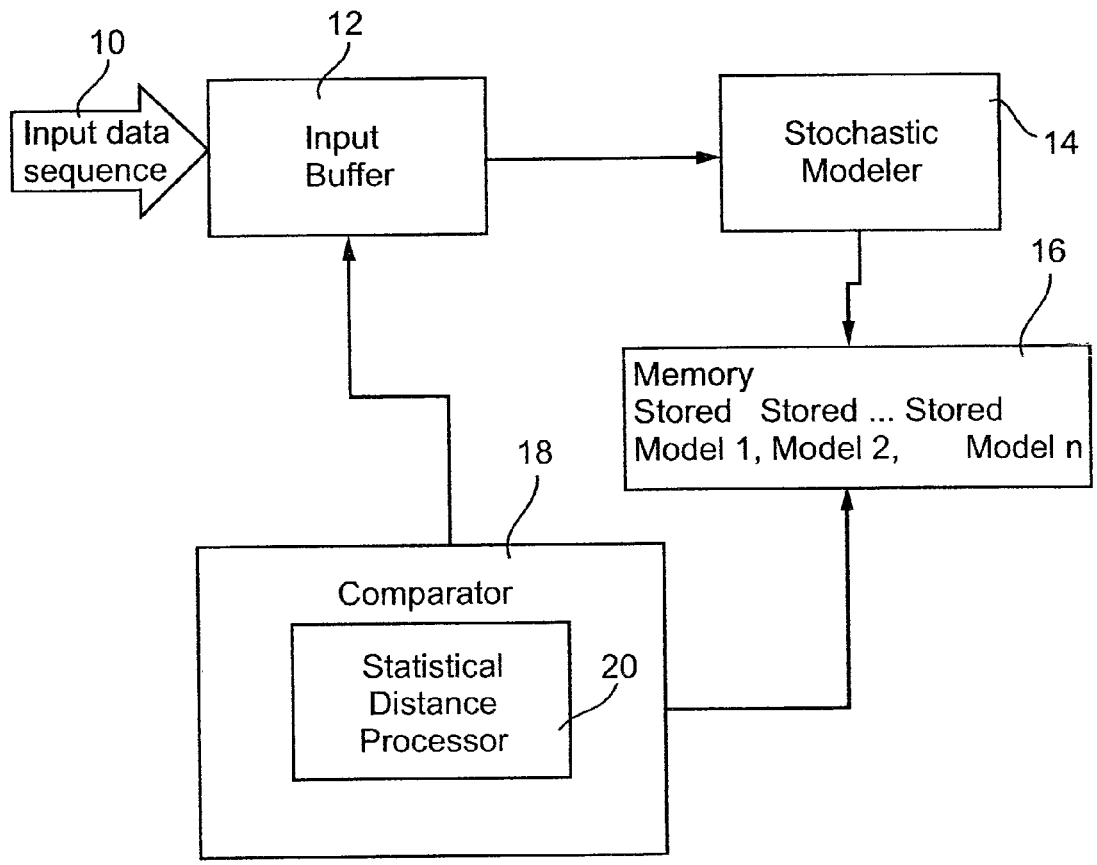
FIG. 2 is a block diagram of a device for monitoring an input sequence according to a first preferred embodiment of the present invention.

Reference is now made to FIG. 2, which is a simplified block diagram showing a generalized embodiment of the present invention. In the embodiment of FIG. 2, an input data sequence 10 arrives at an input buffer 12. A stochastic modeler 14 is able to use the data arriving in the buffer to build a statistical model or measure that characterizes the data. The building process and the form of the model will be explained in detail below.

The modeler 14 does not necessary build models for all of the data. During the course of processing it may build a single model or it may build successive models on successive parts of the data sequence. The model or models are stored in a memory 16. A comparator 18 comprises a statistical distance processor 20, which is able in one embodiment to make a statistical distance measurement between a model generated from current data and a prestored model. In a second embodiment the statistical distance processor 20 is able to make a statistical distance measurement of the distance between two models generated from different parts of the same data. In a third embodiment, the statistical distance processor 20 is able to make a statistical distance measurement of the distance between a pre-stored model and a data sequence. In either embodiment, the statistical measure is used by the comparator 18 to determine whether or not a statistically significant change in the data sequence has occurred.

As will be described below, the comparator 18 may use the KL statistical distance measure. KL is particularly suitable where the series is stationary and tine dependent. Other measures are more appropriate where the series is space or otherwise dependent.

Figure 3:
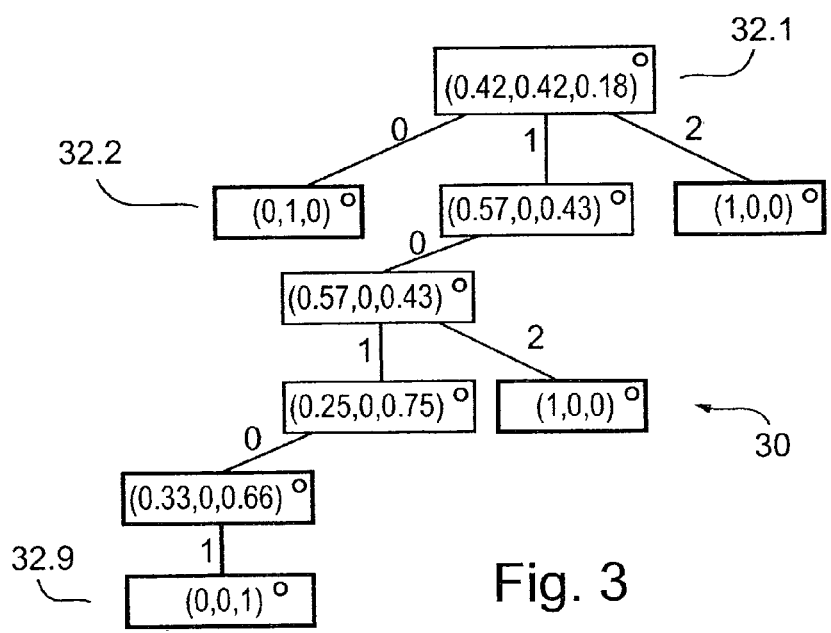
FIG. 3 is a context tree constructed in accordance with an embodiment of the present invention.

Reference is now made to FIG. 3, which is a simplified diagram showing a prior art model that can be used to represent statistical characteristics of data. A context tree 30 comprises a series of nodes 32.1 . . . 32.9 each representing the probability of a given symbol appearing after a certain sequence of previous symbols.

In order to understand the model of FIG. 3, let us firstly consider a sequence (string) of observations $x^N=x_1, \ldots, x_N$, with elements $x_t$, $t=1, \ldots, N$ defined over a finite symbol set, $\chi$, of size d. For example, in process control, a string $x^6$ can represent a sequence of six consecutive observations of the quality level of produced parts: $x^6=a,b,a,c,b,a$. A family of probability measures $P_N(x^N)$, $N=0,1, \ldots$ may be defined over the set $\{\chi^N\}$ of all the stationary sequences of length N, such that a marginality condition $$\sum_{x \in X} P_{N+1}(x^N x) = P_N(x^N) \qquad (2.1)$$

holds for all N; $x^N x = x_1, \ldots, x_N, x$; and $P_0(x^0)=1$ where $x^d$ represents an empty string. For simplification of notation, the sub-index is hereinafter omitted, so that $P_N(x^N) \equiv P(x^N)$.

A finite-memory source model of the sequences defined above, may be provided by a Finite State Machine (FSM). The FSM is characterized by the function $$s(x^{N+1})=f(s(x^N),x_{N+1}) \qquad (2.2)$$

where $s(x^N) \in \Gamma$ are the states with a finite state space $|\Gamma|=S$; $s(x^0)=s_0$ as the initial state; and $f:\Gamma \times \chi \to \Gamma$ being the state transition map of the machine. The FSM is thus defined by $S \cdot (d-1)$ conditional probabilities, the initial state $s_0$, and the transition function. The conditional probability to obtain a symbol from such a finite-memory source is expressed as $$P(x|x^N)=P(x|s(x^N)). \qquad (2.3)$$

A special case of FSM is the Markov process. The Markov process satisfies equation (2.2) above and it is distinguished by the property that for a kth-order Markov process $s(x^N)=x_N, \ldots, x_{N-k+1}$. Thus, reversed strings of a fixed length k act as source states.

Now, the conditional probabilities of a symbol, given all past observations, can only depend on a fixed number of observations k, which number of observations k defines the order of the process. However, even when k is small, a requirement for a fixed order can lead to an inefficient estimation of the probability parameters, since some of the states may in fact depend on shorter (or longer) strings than that specified by k, the process order. Increasing the Markov order, on the other hand, to find a best fit, results in an exponential growth of the number of states, $S=d^k$, and, consequently, of the number of conditional probabilities to be estimated.

A source model which requires less estimation effort than the FSM or Markovian, is that known as the Context-tree source (see Rissanen (1983) and Weinberger, Rissanen and Feder (1995)), the respective contents of which are hereby incorporated by reference. The tree presentation of a finite-memory source is advantageous since states are defined as contexts—graphically represented by branches in the context-tree with variable length—and hence, it requires less estimation efforts than those required for a FSM/Markov presentation. A context-tree is a compact description of the sequenced data generated by a FSM. It is conveniently constructed by the algorithm Context introduced in Rissanen (1983) which is discussed further hereinbelow. The Risanen context algorithm is modified in the present embodiments to consider partial leafs, as will be explained below, which can affect the monitoring performance significantly. The algorithm is preferably used for generating an asymptotically minimal source tree that fits (i.e. describes) the data (see Weinberger, Rissanen and Feder (1995)). Using the above definitions, a description of the context-tree follows. A context-tree is an irreducible set of probabilities that fits the symbol sequence generated by a finite-memory source. The tree assigns a distinguished optimal context for each element in the string, and defines the probability of the element given its optimal context. These probabilities are used later for SPC—comparing between sequences of observations and identifying whether they are generated from the same source. Graphically, the context-tree is a d-ary tree which is not necessarily complete and balanced. Its branches (arcs) are labeled by the different symbol types.

A context, $s(x^t)$, in which the "next" symbol in the string, $x_{t+1}$, occurs is now defined as the reversed string, $$s(x^t) = x_t, \ldots, x_{max\{0, t-k+1\}} \qquad (2.4)$$

for some $k \geq 0$, not necessarily being the same for all strings (the case $k=0$ is interpreted as the empty string $s_0$). The string is truncated since the symbols observed prior to $x_{t-k+1}$ do not affect the occurrence probability of $x_{t+1}$. For a set of optimal contexts, $\Gamma = \{s: \text{shortest contexts satisfying } (2.3)\}$, k is selected to attain the shortest contexts for which the conditional probability of a symbol given the context is practically equal to the conditional probability of that symbol given the whole data, i.e., nearly satisfying equation (2.3) above. Thus, an optimal context, $s \in \Gamma$, acts as a state of the context-tree, in a similar manner to a state in a regular Markov model of order k. However, unlike the Markov model, the lengths of various contexts do not have to be equal and one does not need to fix k such as to account for the maximum context length.

The inconstant context lengths in the context-tree model result in a reduction in the parameters that have to be estimated and, consequently, require less data to identify the source. It is noted, however, that the optimal contexts model does not necessarily satisfy equation (2.2), since the new state $s(x^{N+1})$ can be longer than $s(x^N)$ by more than one symbol (see Weinberger, Rissanen and Feder (1995)).

Each node in the tree preferably contains a vector of conditional probabilities of all symbols $x \in \chi$ given their context (not necessarily optimal), that context being represented by the path from the root to the specific node. Context tree 30 (FIG. 3), is obtained with S=5 optimal contexts, $\Gamma=\{a,c,bac, baba,babab\}$—that are represented respectively by bolded frames nodes 32.2, 32.4, 32.7, 32.8, 32.9—and d=3 symbol types, $\chi=(a,b,c)$. It is noted that, had a Markov chain model of order k=5 been used instead, it would have been necessary to estimate the parameters of $3^5=243$ states (instead of 5 contexts in the context-tree model), although most of them are redundant.

The conditional probabilities of symbols given the optimal contexts, $P(x|s)$ $x \in \chi, s \in \Gamma$, and the marginal probabilities of optimal contexts $P(s)$, $s \in \Gamma$ are preferably estimated by the context algorithm. The joint probabilities of symbols and optimal contexts, $P(x,s), x \in \chi, s \in \Gamma$, represent the context-tree model, and, as will be described in greater detail later on, may be used to derive the CSPC control bounds.

Figure 4:
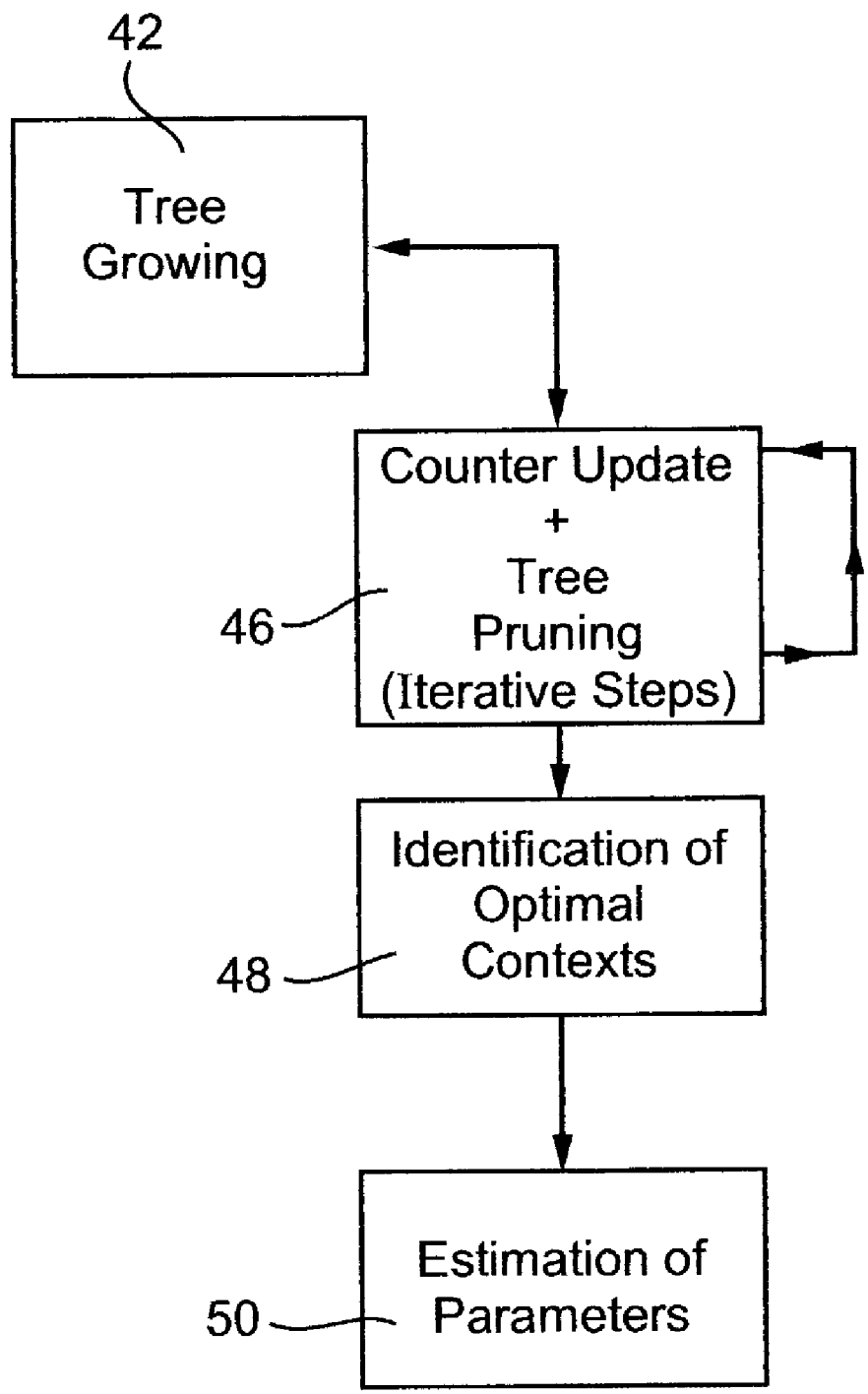
FIG. 4 is a simplified flow diagram showing a process of building an optimal context tree according to embodiments of the present invention.

Reference is now made to FIG. 4, which is a simplified schematic diagram showing stages of an algorithm for producing a context tree according to a first embodiment of the present invention. The construction algorithm of FIG. 4 is an extension of the Context algorithm given in Weinberger, Rissanen and Feder (1995). The algorithm preferably constructs a context-tree from a string of N symbols and estimates the marginal probabilities of contexts and the conditional probabilities of symbols given contexts. The algorithm comprises five stages as follows: two concomitant stages of tree growing 42 and iteratively counter updating and tree pruning 46; a stage of optimal contexts identification 48; and a stage of estimating context-tree probability parameters 50.

In the tree growing stage 42, a counter context-tree, $T_t$, $0 \leq t \leq N$, is grown up to a maximum depth m. Each node in $T_t$ contains d counters—one for each symbol type. The counters, $n(x|s)$, denote the conditional frequencies of the symbols $x \in \chi$ in the string $x^t$ given the context s. Concomitantly with the tree growth stage 42, the counter updating and tree pruning stage 46 ensures that the counter values $n(x|s)$ are updated according to symbol occurrences as will be explained in more detail hereinbelow. The counter context tree is iteratively pruned along with counter updating to acquire the shortest reversed strings, thereby in practical terms to satisfy equation 2.3, it being noted that exact equality is not achieved. In the following stage, selection of optimal contexts 48, a set of optimal contexts $\Gamma$ is obtained, based on the pruned counter context tree. In the estimation stage 50, the estimated conditional probabilities of symbols given optimal contexts $\hat{P}(x|s)$, $x \in \chi, s \in \Gamma$ and the estimated marginal probabilities of optimal contexts $\hat{P}(s)$, $s \in \Gamma$ are derived. As discussed in more detail hereinbelow, both $\hat{P}(x|s)$ and $\hat{P}(s)$ are approximately multinomially distributed and used to obtain the CSPC control limits. The estimated joint probabilities of symbols and optimal contexts, $\hat{P}(x,s)=\hat{P}(x|s)\cdot\hat{P}(s)$, $x \in \chi, s \in \Gamma$, are then derived and represent the context-tree in its final form. It is noted that the term "counter context-tree" is used to refer to the model as it results from the first three stages in the algorithm and the term "context-tree" is used to refer to the result of the final stage, which tree contains the final set of optimal contexts and estimated probabilities.

Returning now to FIG. 2, and once a model is obtained for incoming data, the model is compared by comparator 18 with a reference model, or more than one reference model, which may be a model of earlier received data such as training data or may be an a priori estimate of statistics for the data type in question or the like.

In the following, examples are given based on measurements using the KL statistic. However, the skilled person will appreciated that other statistical measures may be used, including but not restricted to those mentioned hereinabove.

Kullback (1978), the contents of which are hereby incorporated by reference, proposed a measure for the relative 'distance' or the discrimination between, two probability mass functions $Q(x)$ and $Q_0(x)$:

$$K(Q(x), Q_0(x)) = \sum_{x \in X} Q(x) \log \frac{Q(x)}{Q_0(x)} \geq 0 \qquad (3.1)$$

The measure, now known as the Kullback Liebler (KL) measure, is positive for all non-identical pairs of distributions and equals zero iff (if and only if) $Q(x)=Q_0(x)$ for every x. The KL measure is a convex function in the pair $(Q(x),Q_0(x))$, and invariant under all one-to-one transformations of the data. Kullback has shown that the KL distance (multiplied by a constant), between a d-category multinomial distribution $Q(x)$ and its estimated distribution $\hat{Q}(x)$, is asymptotically chi-square distributed with d−1 degrees of freedom:

$$2N \cdot K(\hat{Q}(x), Q(x)) \to \sum_{x \in X} \frac{(n(x) - NQ(x))^2}{NQ(x)} \sim \chi^2_{d-1},$$

where N is the size of a sample taken from the population specified by $Q(x)$; $n(x)$ is the frequency of category (symbol type) x in the sample, $$\sum_{x \in X} n(x) = N;$$

and $\hat{Q}(x) = n(x)/N$ is the estimated probability of category (symbol type) x.

The KL measure for the relative 'distance' between two joint probability mass functions $Q(x,y)$ and $Q_0(x,y)$ can be partitioned into two terms, one representing the distance between the conditioning random variable and the other representing the distance between the conditioned random variable:

$$K(Q(x, y), Q_0(x, y)) = \qquad (3.3)$$

$$\sum_{y \in S} Q(y) \log \frac{Q(y)}{Q_0(y)} + \sum_{y \in S} Q(y) \sum_{x \in X} Q(x|y) \log \frac{Q(x|y)}{Q_0(x|y)}.$$

In the present embodiments the comparator 18 preferably utilizes the KL measure to determine a relative distance between two context-trees. The first tree, denoted by $\hat{P}_i(x,s)$, represents the monitored distribution of symbols and contexts, as estimated from a string of length N at the monitoring time i=1,2, .... The second tree, denoted by $P_0(x,s)$, represents the 'in-control' reference distribution of symbols and contexts. The reference distribution is either known a priori or can be effectively estimated by the context algorithm from a long string of observed symbols as will be discussed in greater detail below. In the latter case, the number of degrees of freedom are doubled.

Utilizing what is known as the minimum discrimination information (MDI) principle (see Alwan, Ebrahimi and Soofi (1998)), the contents of which are herein incorporated by reference, the context algorithm preferably generates a tree of the data being monitored, the tree having a similar structure to that of the reference tree. Maintaining the same structure for the current data tree and the reference tree permits direct utilization of the KL measure.

Now, new observations are constantly being collected and may be used for updating the current data tree, in particular the counters thereof and thus updating the statistics represented by the tree. A significant change in the structure of the tree may be manifested in the tree counters and the resulting probabilities.

Using equation (3.3) above, it is possible to decompose the KL measured distance between the current data context-tree and the reference context-tree (both represented by the joint distributions of symbols and contexts) into a summation involving two terms as follows:

$$K(\hat{P}_i(x, s), P_0(x, s)) = \qquad (3.4)$$

$$\sum_{s \in \Gamma} \hat{P}_i(s) \log \frac{\hat{P}_i(s)}{P_0(s)} + \sum_{x \in \Gamma} \hat{P}_i(s) \sum_{x \in X} \hat{P}_i(x|s) \log \frac{\hat{P}_i(x|s)}{P_0(x|s)}.$$

Of the two terms being summated, one measures the KL distance between the trees' context probabilities, and the other measures the KL distance between the trees' conditional probabilities of symbols given contexts.

Under the null hypothesis that the monitored tree $\hat{P}_i(x,s)$ is generated from the same source that generated, $P_0(x,s)$ and by using the multinomial approximation referred to above, it is possible to derive an asymptotic probability density function of the KL measure between $\hat{P}_i(x,s)$ and $P_0(x,s)$, i.e., $$K(\hat{P}_i(x, s), P_0(x, s)) \to \frac{1}{2N}\chi^2_{S-1} + \sum_{s \in \Gamma} \hat{P}_i(s) \cdot \frac{1}{2n(s)} \chi^2_{d-1} = \qquad (3.5)$$

$$\frac{1}{2N}\chi^2_{S-1} + \sum_{s \in \Gamma} \frac{n(s)}{N} \cdot \frac{1}{2n(s)} \chi^2_{d-1} =$$

$$\frac{1}{2N}\chi^2_{S-1} + \frac{1}{2N} \sum_{s \in \Gamma} \chi^2_{d-1} =$$

$$\frac{1}{2N}(\chi^2_{S-1} + \chi^2_{S(d-1)}) = \frac{1}{2N}\chi^2_{Sd-1},$$

where $n(s)$ is the frequency of an optimal context $s \in \Gamma$ in the string; N is the size of the monitored string; S is the number of optimal contexts; and d is the size of the symbol set. As mentioned above, if the reference tree has to be estimated, the number of degrees of freedom is doubled. Thus, the KL statistic for the joint distribution of the pair $(\chi, \Gamma)$ is asymptotically chi-square distributed with degrees of freedom depending on the number of symbol types and the number of optimal contexts. The result is of significance for the development of control charts for state-dependant discrete data streams based on the context-tree model.

Now, given a type I error probability $\alpha$, the control limits for the KL statistic are given by, $$0 \leq 2N \cdot K(\hat{P}_i(x,s), P_0(x,s)) \leq \chi^2_{Sd-1,1-\alpha}. \qquad (3.6)$$

Thus, the upper control limit (UCL) is the 100(1−α) percentile of the chi-square distribution with (Sd−1) degrees of freedom.

The control limit (3.6) has the following, advantageous, characteristics:

i) It is a one-sided bound; if the KL value is larger than the UCL, the process is assumed to be 'out-of-control' for a given level of significance.

ii) The control limit lumps together all the parameters of the context-tree, in contrast with traditional SPC where each process parameter is controlled separately. Nevertheless, the KL statistic of the tree can be easily decomposed to monitor separately each node in the context-tree. This can be beneficial when looking for a cause of an 'out-of-control' signal.

iii) If Sd is large enough the KL statistic is approximately normally distributed. Hence, conventional SPC charts can be directly applied to monitor the proposed statistic.

A basic condition for applying the KL statistic to sample data requires that $P_0(x|s)>0$, $\forall x \in \chi$, $\forall s \in \Gamma$. Such a constraint may be satisfied with the predictive approach, i.e., $$\hat{P}(x|s) = \frac{n(x|s) - \sum_{b \in X} n(x|sb) + 1/2}{n(s) + d/2} \quad \forall x, b \in X, s \in \Gamma$$

where all probability values assigned to any of the symbol types are strictly positive, in contrast to the non-predictive approach:

$$\hat{P}(x|s) = \frac{n(x|s) - \sum_{b \in X} n(x|sb)}{n(s)} \quad \forall x, b \in X, s \in \Gamma$$

by defining $$\frac{0}{0} \equiv 0.$$

Figure 5A:
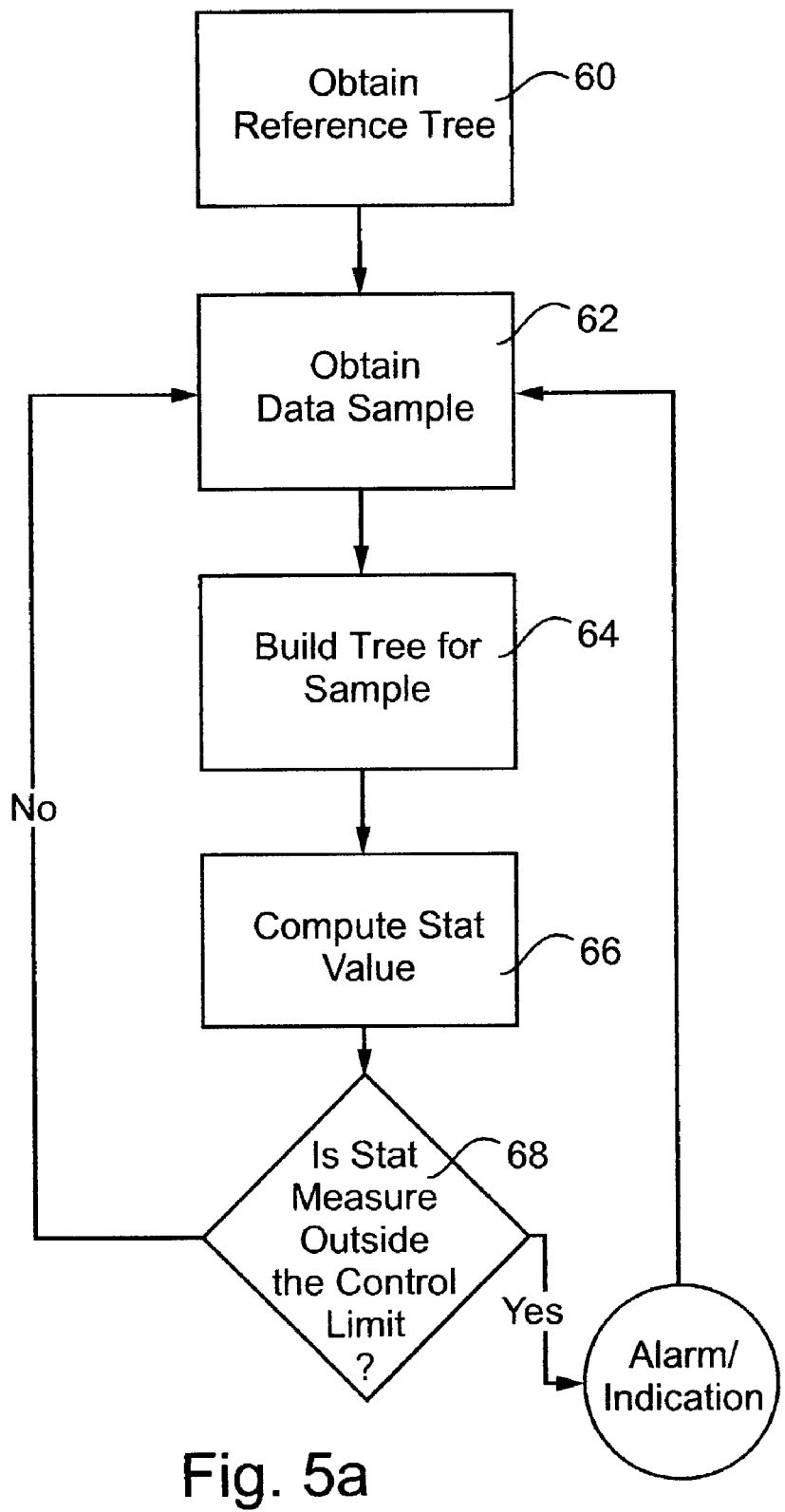
FIG. 5 is a simplified flow diagram showing a process of monitoring using embodiments of the present invention.

The choice among these alternative procedures, depends both on the knowledge regarding the system states and on the length of the string used to construct the context-tree. However, in the latter non-predictive case, the number of degrees of freedom is adapted according to the number of categories that are not equal to zero, thus, subtracting the zero-probability categories when using the non-predictive approach. Reference is now made to FIG. 5A, which is a simplified flow chart illustrating the control procedure used by the device of FIG. 2 to control a process or the like. In FIG. 5, a first stage 60 comprises obtaining a reference context-tree, $P_0(x,s)$. This may be done analytically or by employing the context algorithm to a long string of representative data, for example from a training set, or the model may be obtained from tin external source.

In a second stage 62, a data source is monitored by obtaining data from the source. At succeeding points, a data sample is used to generate a current data tree $\hat{P}_t(x,s)$ from a sample of sequenced observations of size N. The sample size preferably complies with certain conditions, which will be discussed in detail hereinbelow. The sequences can be mutual-exclusive, or they can share some data points (often this is referred to as "sliding window" monitoring). The order of the sequence can be reorganize or permute in various ways to comply with time-dependent constraints or other type of side-information, which is available. Each sequence used to generate a model is referred to hereinbelow as a "run" and contributes a monitoring point in the CSPC chart. Following the MDI principle referred to above, the structure of the current data tree is selected to correspond to the structure of the reference context-tree. Once the structure of the tree has been selected, then, in a model building stage 64, the counters of the current data context tree are updated using values of the string, and probability measures of the monitored context-tree are obtained, as will be explained in greater detail below.

Once the model has been built then it may be compared with the reference model, and thus the KL value can be calculated to give a distance between the two models in a step 66. As mentioned above, the KL value measures a relative distance between the current model, and thus the monitored distributions $\hat{P}_t(x,s)$ and the reference distributions $\hat{P}_0(x,s)$ as defined in the reference model. In some cases it might be valuable to use several distance measures simultaneously and interpolate or average their outcomes.

The KL statistic value is now plotted on a process control chart against process control limits in a query step 68. The control limits may for example comprise the upper control limit (UCL) given in equation (3.6) above. If the KL value, or like alternative statistic, is larger than the UCL it indicates that a significant change may have occurred in the process and preferably an alarm is set.

The process now returns to step 62 to obtain a new run of data, and the monitoring process is repeated until the end of the process.

Considering FIG. 5A in greater detail, the data sample obtained at stage 62 may be considered as a sequence of observations $x^N = x_1, \ldots, x_N$, with elements $x_t$ $t=1,\ldots,N$ defined over a finite symbol set, $\chi$, of size d. In stage 64, a primary output is a context tree $T_N$ for the sample, which context tree contains optimal contexts and the conditional probabilities of symbols given the optimal contexts. Namely it is a model of the incoming data, incorporating patterns in the incoming data and allowing probabilities to be calculated of a likely next symbol given a current symbol.

Figure 5B:
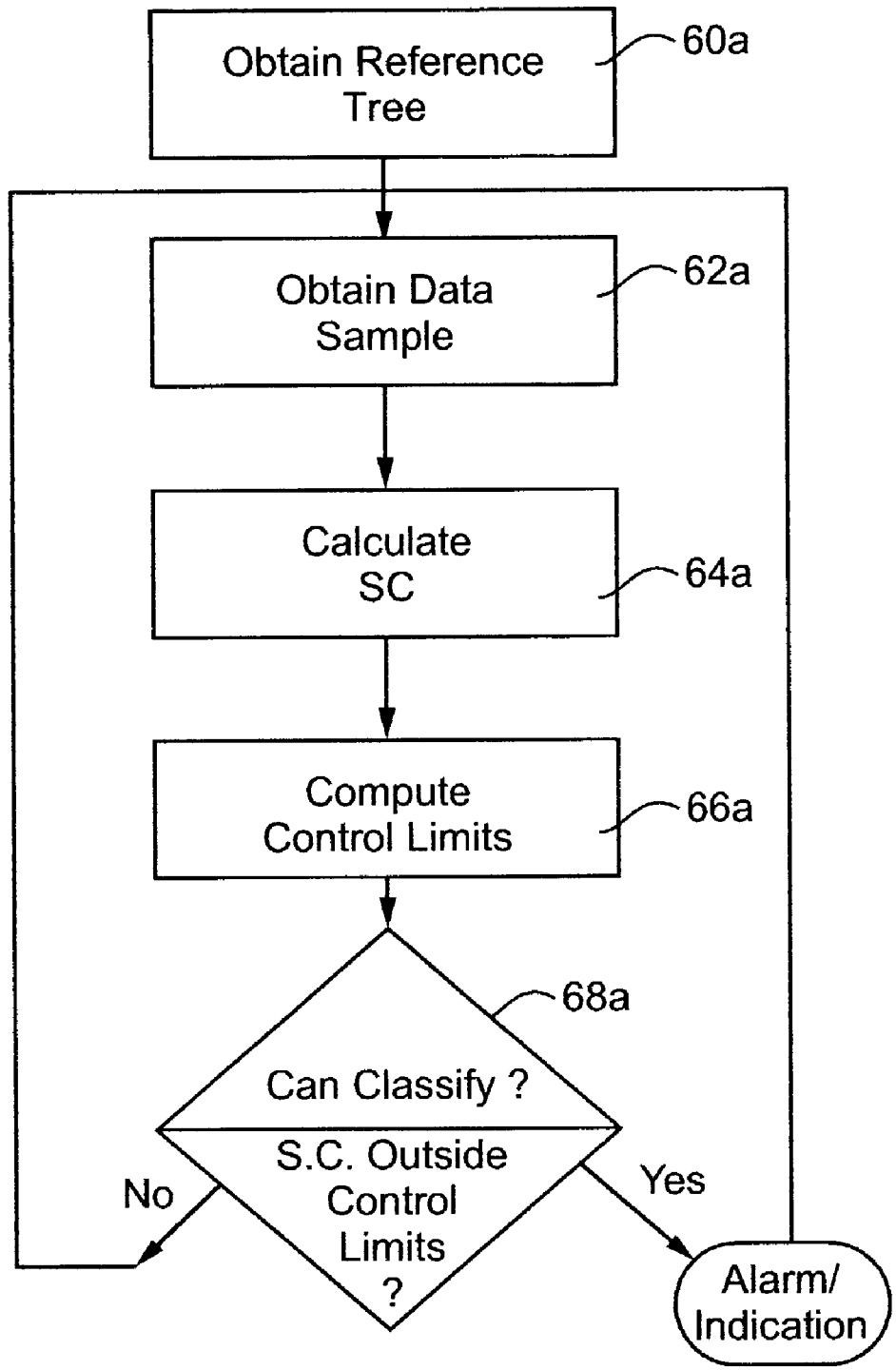

Reference is now made to FIG. 5B, which is a simplified flow chart showing how the same measurement may be carried out using stochastic complexity. A reference tree is initially obtained in step 60A. Then a data sample is obtained in step 62A. Stochastic complexity is calculated in step 64A and control limits are calculated in step 66A. Finally the sample values are tested in step 68A to determine whether the stochastic complexity is within the control limits.

Figure 6A:
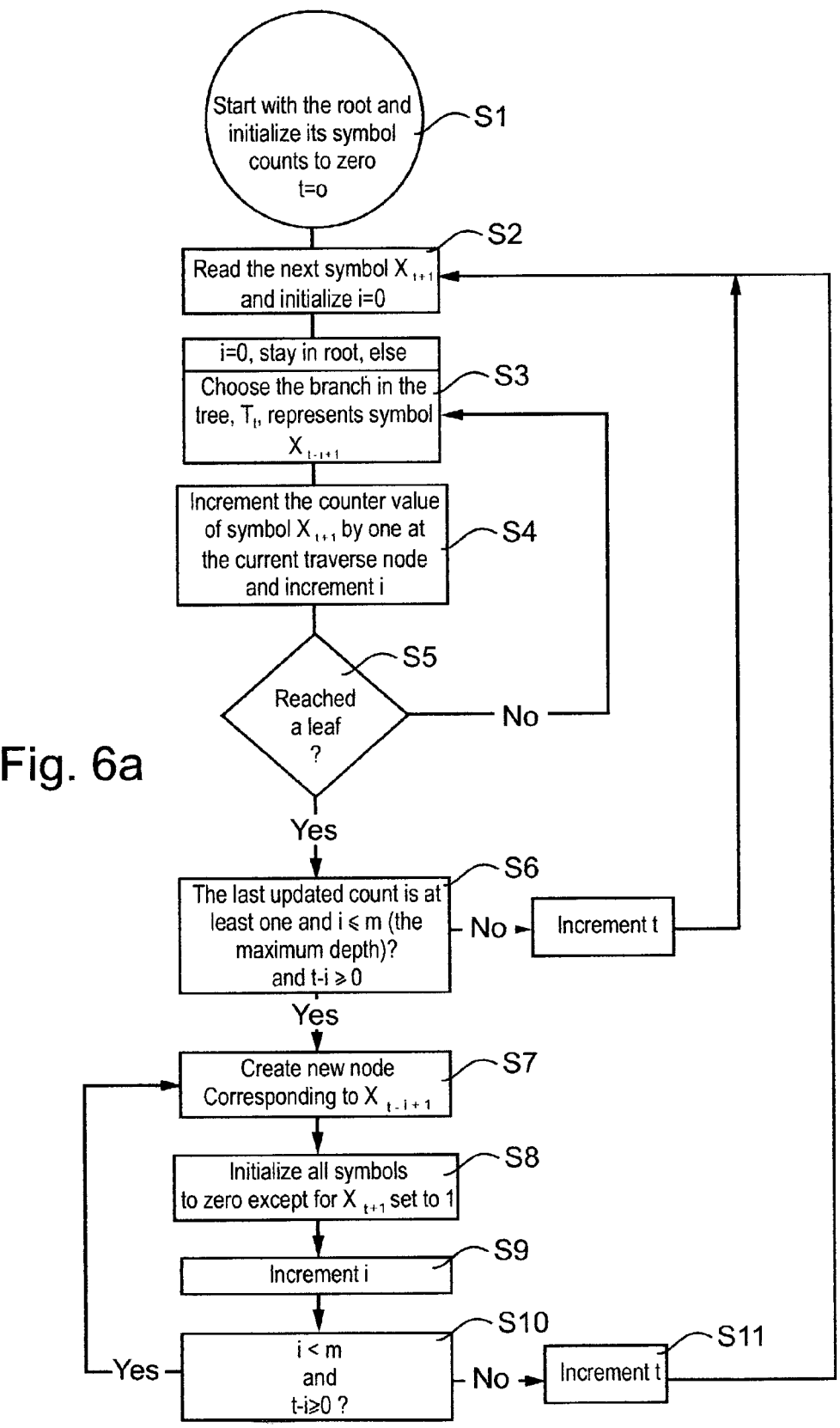
FIG. 6A is a simplified flow diagram showing the procedure for building up nodes of a context tree according to a preferred embodiment of the present invention.

Reference is now made to FIG. 6A, which is a simplified flow chart showing an algorithm for carrying out stage 64 in FIG. 5, namely building of a context tree model based on the sample gathered in step 62. More specifically, FIG. 6A corresponds to stages 42 and 46, in FIG. 4. The tree growing algorithm of FIG. 6A constructs the tree according to the following rules (the algorithm depends on parameters that can be modified and optimized by the user):

A stage S1 takes a single root as the initial tree, $T_0$, and all symbol counts are set to zero. Likewise a symbol counter t is set to 0.

A stage S2 reads a $(t+1)^{th}$ symbol from the input sequence, thus, in the first iteration, $x_{t+1} = x_1$ is being read.

In stage S3 the algorithm begins a process of tracing back from a root node to the deepest node in the tree. If i=0 then tracing remains within the same root, otherwise the algorithm chooses the branch $T_t$ representing symbol $x_{t-i+1}$. Stage S4 is part of the traceback process of step S3. As each node in the tree is passed, the counter at that node, corresponding to the current symbol, is incremented by one.

In step S5, the process determines whether it has reached a leaf, i.e., a node with no descendents nodes. If so, the process continues with S6, otherwise it returns to S3.

S6 controls the creation of new nodes. S6 checks that the last updated counter is at least one and that further descendents nodes can be opened. It will, for example, detect a counter set to zero in step S8. Preferably, the last updated count is at least 1, i≦m(the maximum depth) and t−i≧0. Step S7 creates a new node corresponding to $x_{t-i+1}$. Step S8 generates one counter with value 1 and the other counters with zero value at new node creation. Those values may be detected by S6 when another symbol is read. Step S10 controls the retracing procedure needed to stimulate tree growth to its maximal size, by testing i≦m and t−1≧0 and branching accordingly.

Once a leaf has been reached in S5 or S10, then the traceback procedure is complete for the current symbol. The maximal allowed deepest node is set at an arbitrary limit (e.g. 5) to limit tree growth and size, and save computations and memory space. Without such a limit there would be a tendency to grow the tree beyond a point which is very likely to be pruned in any case.

Stage S6 thus checks whether the last updated count is at least one and if maximum depth has yet been reached. If the result of the check is true, then a new node is created in step S7, to which symbol counts are assigned, all being set in step S8 to zero except for that corresponding to the current symbol, which counter is set to 1. The above procedure is preferably repeated until a maximum depth is reached or a context $x_t x_{t+1} \ldots x_i$ is reached in stage S10. Thereafter the next symbol is considered in stage S2.

More specifically, having recursively constructed an initial tree $T_t$ from an initial symbol or string $x^t$, the algorithm moves ahead to consider the next symbol $x_{t+1}$. Then tracing back is carried out along a path defined by $x_t, x_{t-1}, \ldots$ and in each node visited along the path, the counter value of the symbol $x_{t+1}$ is incremented by 1 until the tree's current deepest node, say $x_t, \ldots, x_{t-l+1}$, is reached. Although not shown in FIG. 6A an initial string preceding $x^t$ may be used in order to account for initial conditions (see Rissanen 1983, the contents of which are hereby incorporated by reference).

If the last updated count is at least 1, and l<m, where m is the maximum depth, the algorithm creates new nodes corresponding to $x_{t-r}$, l<r≦m, as descendent nodes of the node defined in S6. The new node is assigned a full set of counters, which are initialized to zero except for the one counter corresponding to the current symbol $x_{t+1}$, which is set to 1. Retracing is continued until the entire past symbol history of the current input string has been mapped to a path for the current symbol $x_{t+1}$ or until m is reached, r being the depth of the new deepest node, reached for the current path, after completing stage S7.

Figure 6B:
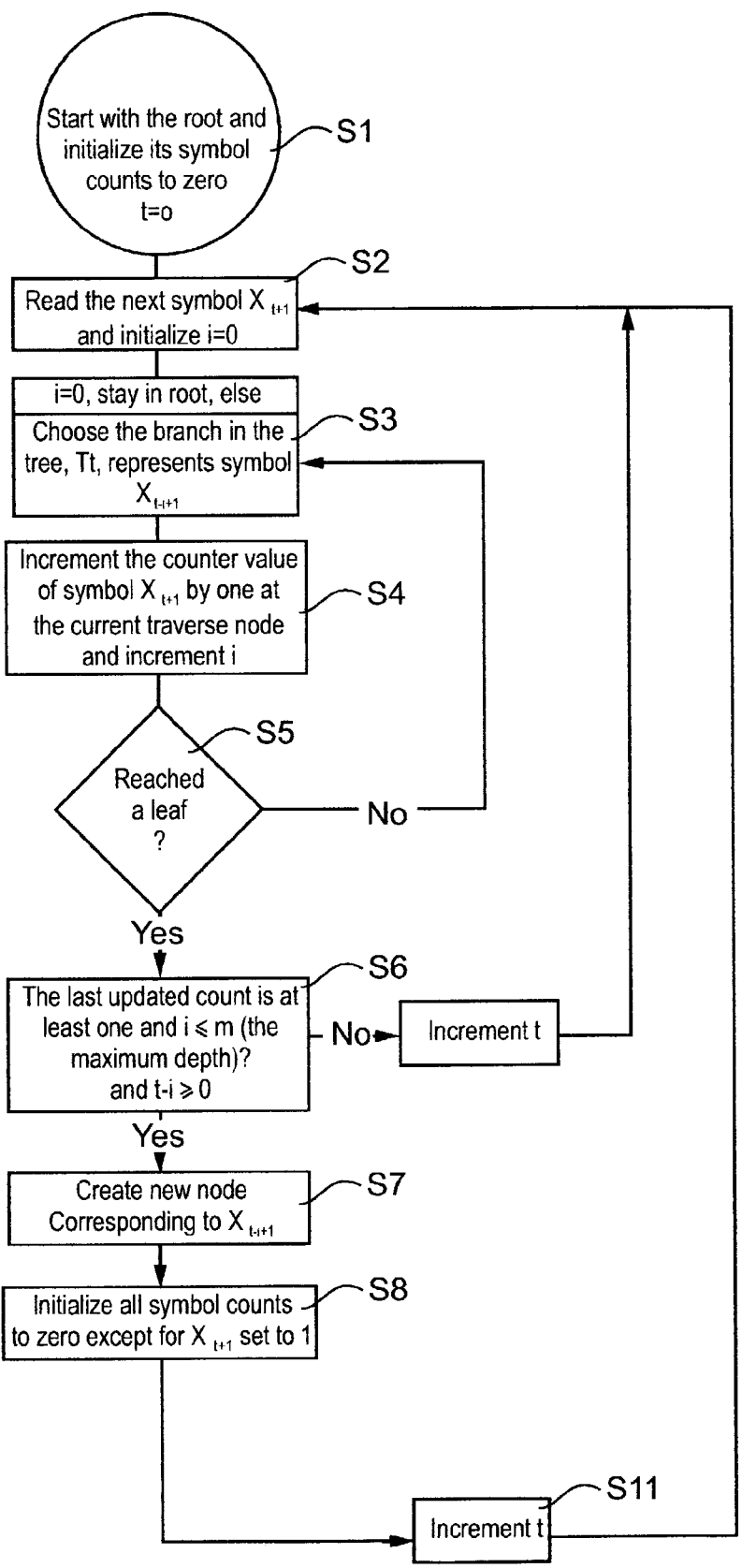
FIG. 6B is a simplified flow chart illustrating a variation of FIG. 6A for more rapid tree growth.

Reference is now made to FIG. 6B, which is a simplified flow chart showing a variation of the method of FIG. 6A. Steps that are the same as those in FIG. 6A are given the sane reference numerals and are not referred to again except as necessary for understanding the present embodiment.

In FIG. 6B, the steps S9 and S10 are removed, and step S8 is followed directly by step S11, thereby to reduce the computational complexity. While the previous algorithm is more accurate, in this algorithm, the tree grows slowly—at most one new node per symbol. Thus in the beginning—when the tree has not yet grown to its maximal depth—some counts are lost. If the sequence length is much longer compared to the maximal tree depth, than the difference in the counter values produced by both algorithms will be practically insignificant for the nodes left after the pruning process.

In order to understand better the algorithms of FIG. 6, reference is now made to FIGS. 7-9 which are diagrams of a model being constructed using the algorithm of FIG. 6. Further illustrations are given in Tables A1 and A2.

In FIGS. 7-9, tree 100, initially comprises a root node 102 and three symbol nodes 104-108. Each one of nodes 102-108 has three counters, one for each of the possible symbols "a", "b" and "c". The counters at the root node give the numbers of appearance of the respective symbols and the counters at the subsequent, or descendent, nodes represent the numbers of appearances of the respective symbol following the symbol path represented by the node itself. Thus the node 104 represents the symbol path "a". The second counter therein represents the symbol "b". The counter being set to 1 means that in the received string so far the number of "b"s following an "a" is 1. Node 106 represents the symbol path "b" and the first counter represents the symbol "a". Thus the first counter being set to "1" means that in the received string so far the symbol "a" has appeared once following a "b". The second counter being on "0" implies that there are no "b"s followed by "b"s.

Node 108 represents the context "b a" corresponding to the symbol path or the sequence "a b" (contexts are written in reverse order). The first counter, representing "a" being set to "1" shows that there is one instance of the sequence "a b" being followed by "a".

In FIG. 8, a fourth symbol $x_4 = b$ is received. The steps S3 to S10 of FIG. 6 are now carried out. The symbol b, as preceded by "a b a" in that order can be traced back from node 104 to 102, (because the traceback covers the "b a" suffix of the sequence). The "b" counters are incremented at each node passed in the traceback. Likewise the sequence "a b a" can be traced back from node 108 to the root, again incrementing the "b" counters each time.

In FIG. 9, a new node 110 is added after node 104, representing step S7 of FIG. 6. The node is assigned three counters as with all previous nodes. The "b" counter thereof is set to 1 and all other counters are set to "0" as specified in step S8 of FIG. 6. It is noted that the context for the new node is "a b", thus, representing the sequences "b a".

Returning now to the tree pruning stage 46 of FIG. 4, it is necessary to prune the tree, as will be described below, to obtain what may be referred to as the optimal contexts of $T_N$. Tree pruning is achieved by retaining the deepest nodes w in the tree that practically satisfy equation 2.3 above. The following two pruning rules apply (see Weinberger, Rissanen and Feder (1995) for further details):

Pruning rule 1: the depth of node w denoted by |w| is bounded by a logarithmic ratio between the length of the sting and the number of symbol types, i.e., |w|≦log(t+1)/log(d); and, Pruning rule 2: the information obtained from the descendant nodes, sb ∀b∈χ, compared to the information obtained from the parent node s, is larger than a 'penalty' cost for growing the tree (i.e., of adding a node).

The driving principle is to prune any descendant node having a distribution of counter values similar to that of the parent node. In particular, we calculate $\Delta_N(sb)$, a measure of the (ideal) code-length-difference of the descendant node sb, ∀b∈χ, $$\Delta_N(sb) = \sum_{x \in X} n(x|sb) \log\left(\frac{\hat{P}(x|sb)}{\hat{P}(x|s)}\right) \quad (4.1)$$

and then require that $\Delta_N(w) \geq C(d+1)\log(t+1)$, wherein logarithms are taken to base 2; and C is a pruning constant tuned to process requirements (with default C=2 as suggested in Weinberger, Rissanen and Feder (1995)).

The tree pruning process is extended to the root node with condition $\Delta_N(x^0) = \infty$, which condition implies that the root node itself cannot be pruned.

Figure 10:
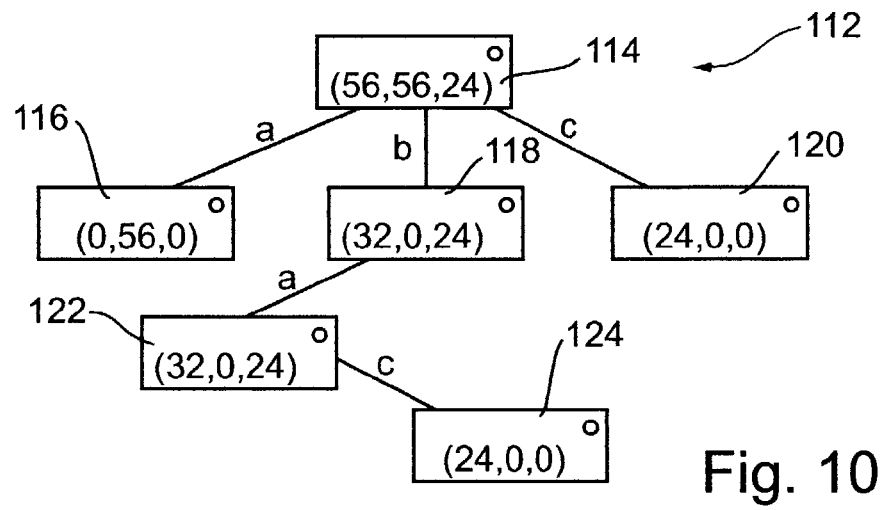

Reference is now made to FIG. 10, which is a simplified diagram showing a pruned counter context-tree 112 constructed by applying the tree building of FIG. 6 followed by tree pruning on a string containing 136 symbols—eight replications of the sub string: (a,b,a,b,c,a,b,a,b,c,a,b,a,b,a,b,c).

The tree comprises a root node 114 and five further nodes 116-124. By contrast, the unpruned tree, from which this was taken, may typically have had three daughter nodes for each node.

Returning again to FIG. 4, and stage 48, identification of optimal contexts, is now described in greater detail. In stage 48, a set of optimal contexts, $\Gamma$, containing the S shortest contexts satisfying equation 2.3 is specified. An optimal context can be either a path to a leaf (a leaf being a node with no descendants) or a partial leaf in the tree. A partial leaf is defined for an incomplete tree as a node which is not a leaf. Now, for certain symbol(s) the path defines an optimal context satisfying equation 2.3, while for other symbols equation 2.3 is not satisfied and a descendant node(s) is created. The set of optimal contexts is specified by applying the following rule:

$$\Gamma = \left\{ s : \sum_{x \in X} \left( n(x \mid s) - \sum_{b \in X} n(x \mid sb) \right) > \omega \right\} \forall s \in T_t, \quad (4.2)$$

where $\omega=0$ is the default. This means that $\Gamma$ contains only those contexts that are not part of longer contexts. When the inequality in expression 4.2 turns into equality, that context is fully contained in a longer context and, thus, is not included in $\Gamma$. It is noted that in each level in the tree there is a context that does not belong to a longer context and, therefore, does not satisfy equation 4.2. This is generally due to initializing conditions. Such inconsistency can be solved by introducing an initiating symbol string as suggested in Weinberger, Rissanen and Feder (1995).

In summary, $\Gamma$ contains all the leaves in the tree as well as partial leaves satisfying equation 4.2 for certain symbols.

Returning to FIG. 10, and node 122 corresponds to string history or context s=ba and is, as defined above, a partial leaf (acts as an optimal context) for symbols a and c. This is firstly because the longer context s=bac does not include all symbol occurrences of symbols a and c. Secondly, the contexts bab and baa were pruned and lumped into the context ba. Applying equation 4.2 to the pruned counter context-tree presented in FIG. 10 results in four optimal contexts $\Gamma=\{a; bac; c; ba\}$. The first three contexts in $\Gamma$ are leaves, the latter is a partial leaf and defines an optimal context for symbols a and c. Considering now in greater detail stage 50, estimation of parameters in FIG. 4, the estimation stage is composed of three steps as follows:

1) the probabilities of optimal contexts are estimated and denoted by $\hat{P}(s)$, $s \in \Gamma$;
2) the conditional probabilities of symbols given the optimal contexts are estimated and denoted by $\hat{P}(x|s)$, $x \in \chi$, $s \in \Gamma$; and
3) the estimated joint probabilities of symbols and optimal contexts are calculated $\hat{P}(x,s)$, $x \in \chi$, $s \in \Gamma$.

Given the set of optimal contexts and the pruned counter tree, the probability of optimal contexts in the tree, $\hat{P}(s)$, $s \in \Gamma$, are estimated by their frequency in the string:

$$\hat{P}(s) = \frac{n(s)}{\sum_{s \in \Gamma} n(s)} = \frac{\sum_{x \in X} \left( n(x \mid s) - \sum_{b \in X} n(x \mid sb) \right)}{\sum_{s \in \Gamma} \sum_{x \in X} \left( n(x \mid s) - \sum_{b \in X} n(x \mid sb) \right)} \forall x \in X, s \in \Gamma$$

where n(s) is the sum of the symbol counters in the corresponding leaves (or partial leaves) that belong to the optimal context s and not to a longer context sb $b \in \chi$. Each symbol in the string thus belongs to one out of S disjoint optimal contexts, each of which contains n(s) symbols. An allocation of symbols of a sufficiently long string to distinctive optimal contexts can be approximated by the multinomial distribution.

Returning to FIG. 10, and the estimated probabilities of optimal contexts in FIG. 6 are given respectively by, $$\{\hat{P}(a), \hat{P}(bac), \hat{P}(c), \hat{P}(ba)\} = \{56/136, 24/136, 24/136, 32/136\}.$$

Once the symbols in the string are partitioned to S substrings of optimal contexts, the conditional probabilities of symbol types given an optimal context are estimated by their frequencies in the respective substring, $$\hat{P}(x \mid s) = \frac{n(x \mid s) - \sum_{b \in X} n(x \mid sb)}{n(s)} \forall x, b \in X, s \in \Gamma \quad (4.3)$$

where $$\frac{0}{0} \equiv 0.$$

The distribution of symbol types in a given optimal context is, thus, approximated by another multinomial distribution.

An alternative predictive approach to equation 4.3 was suggested in Weinberger, Rissanen and Feder (1995). It is implemented in cases where one needs to assign strictly positive probability values to outcomes that may not actually have appeared in the sample string, yet can occur in reality. Thus, $$\hat{P}(x \mid s) = \frac{n(x \mid s) + 1/2}{\sum_{x \in X} n(x \mid s) + d/2} \forall x \in X, s \in \Gamma \quad (4.4)$$

The choice among the two alternative procedures above depends both on the knowledge regarding the system states and on the length of the string used to construct the context-tree. The latter approach is suitable for applications involving forecasting.

Figure 11:
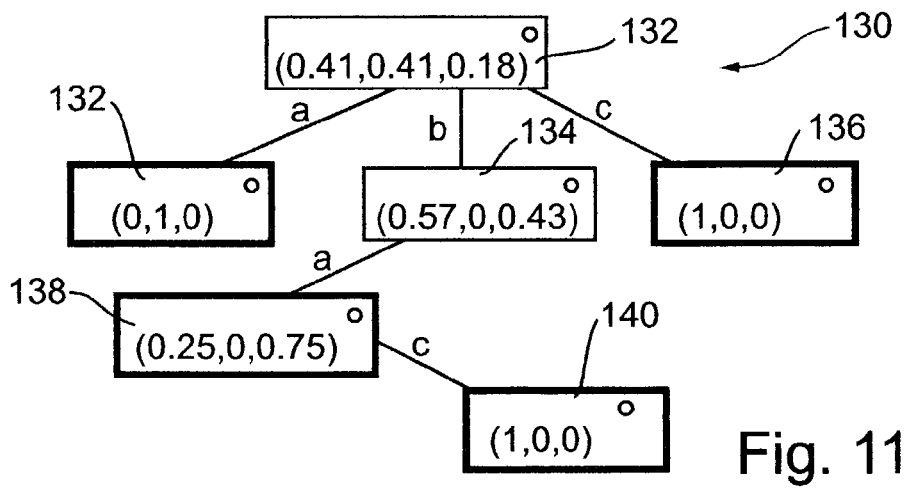

Reference is now made to FIG. 11, which is a simplified tree diagram showing a tree 130 having a root node 132 and five other nodes 134-140. The counters now contain probabilities, in this case the estimated conditional probabilities of symbols given contexts. The probability estimates are generated by applying equation 4.3 to the counter context-tree 112 of FIG. 11. For example, the conditional probability of a symbol type $x \in \{a,b,c\}$ given the context s=a, is estimated as $\hat{P}(x|a)=(0,56/56,0)=(0,1,0)$, whereas the conditional probabilities of a symbol $x \in \{a,b,c\}$ given the context s=ba is estimated as $\hat{P}(x|ba)=(8/32,0,24/32)=(0.25,0,0.75)$. The probabilities of symbols in non-optimal contexts are also shown for general information.

As shown in the figure the optimal contexts are {132,140, 136,138}.

Returning now to FIG. 3, tree 30 is the context tree generated from a string of length N=1088 (64 replications of the basic string a,b,a,b,c,a,b,a,b,c,a,b,a,b,a,b,c). The maximum tree depth has increased from three to five levels, as opposed to the preceding examples. Nevertheless, the number of optimal contexts acting as states has only increased from four to five. It is pointed out that had a Markov chain model of order k=5 been used, it would have been necessary to estimate transition probabilities between $3^5=243$ states, most of which are redundant in any case.

The joint probabilities of symbols and optimal contexts that represent the context-tree in its final form are evaluated thus:

$$\hat{P}(x,s)=\hat{P}(x|s)\cdot\hat{P}(s) \; x\in\chi, s\in\Gamma.$$

As explained above with respect to FIG. 5, the model as built in accordance with the procedures outlined in FIGS. 6-11 can be used in the comparison stage of FIG. 5 to obtain information about the comparative statistical properties of data sequences.

The above procedures are summarized and illustrated in the following two tables for string $x^6=4,4,4,3,3,2$ where d=5, $\chi=\{0,1,2,3,4\}$:

TABLE A1

Tree growing and counter updating stage in context algorithm

| Steps | Tree | Description |
|---|---|---|
| Step 0: $T_0$ | Root node (0,0,0,0,0) | Initialization: the root node, $\lambda$, denotes the empty context |
| Step 1: $T_1$<br>$x^1=4$ | Root node (0,0,0,0,1) | The only context for the first symbol is $\lambda$, the counter $n(x=4|\lambda)$ was incremented by one. |
| Step 2: $T_2$<br>$x^2=4,4$ | Root (0,0,0,0,2), $n(x=4|\text{root})=2$; child via 4: (0,0,0,0,1), $n(x=4|s=4)=1$ | The counters $n(x=4|\lambda)$ and $n(x=4|s=4)$ are incremented by one. The node of the context s = 4 is added to accumulate the counts of symbols given the context s = 4. |
| Step 3: $T_3$<br>$x^3=4,4,4$ | Root (0,0,0,0,3), $n(x=4|\text{root})=3$; via 4: (0,0,0,0,2), $n(x=4|s=4)=2$; via 4: (0,0,0,0,1), $n(x=4|s=44)=1$ | The counter of the symbol 4 is incremented by one in the nodes from the root to the deepest node along the path defined by the past observations. In this case, the counters - $n(x=4|\lambda)$ and $n(x=4|s=4)$ are incremented by 1. A new node is added for the context s = 44. And $n(x-4|s=44)=1$. |
| Stage 4: $T_4$<br>$x^4=4,4,4,3$ | Root (0,0,0,1,3), $n(x=3|\text{root})=1$; via 4: (0,0,0,1,2), $n(x=3|s=4)=1$; via 4: (0,0,0,1,1), $n(x=3|s=44)=1$; via 4: (0,0,0,1,2), $n(x=3|s=444)=1$ | The counters - $n(x=4|\lambda)$, $n(x=4|s=4)$ and $n(x=4|s=44)$ are incremented by one since the past contexts are $s=\lambda$, $s=4$, $s=44$. A new node is added for the context s = 444 of the observation $x_4=3$. |
| Stage 5:<br>$x^5=\ldots,4,3,3$ | Root (0,0,0,2,3), $n(x=3|\text{root})=2$; via 3: (0,0,0,1,0), $n(x=3|s=3)=1$; via 4: (0,0,0,1,2), $n(x=3|s=4)=1$; under s=3 via 4: (0,0,0,1,0), $n(x=3|s=34)=1$; under s=4 via 4: (0,0,0,1,1), $n(x=3|s=44)=1$; via 4: (0,0,0,1,0), $n(x=3|s=444)=1$ | Add new nodes for the contexts s = 3, s = 34, s = 344 . . . . Update the counter of the symbol x = 3 from the root to the deepest node on the path of past observations. |

TABLE A1-continued

Tree growing and counter updating stage in context algorithm

| Steps | Tree | Description |
|---|---|---|
| Stage 6: $x^6 = \ldots, 3,3,2$ | (tree diagram with root $n(x=2|root)=1$, $(0,0,1,2,3)$, branching to $(0,0,2,1,0)$ and $(0,0,0,1,2)$, further to $(0,0,0,1,0)$, $(0,0,0,1,0)$, $(0,0,0,1,1)$, and $(0,0,0,1,0)$; with $n(x=2|s=33)=1$, $n(x=3|s=34)=1$, $n(x=3|s=444)=1$) | Update the counter of the symbol $x = 2$ from the root to the deepest node on the path of past observations. Add the contexts: $s = 33$ and so on. | for string $x^6 = 4,4,4,3,3,2$

TABLE A2

Pruning stage in context algorithm for the string

| Rule | Tree | Description |
|---|---|---|
| Rule 1: | O $(0,0,0,0,0)$ | Rule 1:<br>Maximum tree Depth $\leq \log(t)/\log(d) = \log(6)/\log(5) = 1.11$<br>The maximum tree depth is of level one. Thus, all nodes of level 2 and below are trimmed. |
| Rule 2: | O $(0,0,0,0,1)$ | Rule 2: for the rest of the nodes in level one and the root, we apply trimming rule 2. The threshold for $C = 2$ is:<br>$\Delta_6(u) > 2(d + 1)\log(t + 1) = 33.7$<br>And for each of the nodes:<br>$$\Delta_6(sb = \lambda 3) = 0 + 0 + 1 \cdot \log\left(\frac{0.5}{1/6}\right) + 1 \cdot \log\left(\frac{0.5}{2/6}\right) + 0 = 2.17$$<br>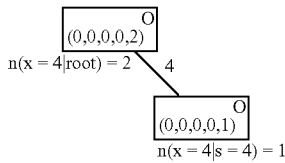<br>The code-length difference is below the threshold, hence the first level nodes are trimmed. |

$x^6 = 4,4,4,3,3,2$

Predictive vs. Non Predictive models: Predictive models assign non-zero probabilities to events that were never observed in the training set, while non-predictive models assign zero probability to events that were never observed in the training set. The choice of the appropriate model is based on the feasibility of the un-observed events: if unobserved events are not feasible, than the non-predictive formula is more accurate. Once again, the use of predictive vs non predictive models can be checked against cross-validation properties.

Selection of the tree truncation threshold the threshold is one of the most important default parameters and directly determines the size of the final model. Indirectly it determines the computational aspects of the algorithm, and the accuracy of the model. It may be optimized for each application. For example, in predictive applications such as time series forecasting it was empirically found that a smaller than default threshold improves the quality of the prediction.

Tree Construction Parameter: The tree construction parameters proposed in the algorithm are default parameters for optimization. Such parameters include: i) the tree maximum depth; ii) the algorithm buffer size; iii) values of pruning constants; iv) the default parameters in accordance with the conditions of each specific application; vi) the number of nodes to grow after a leaf is reached; vii) other parameters indicated in FIG. 6A etc.

NUMERICAL EXAMPLE

To assess the effectiveness of the suggested CSPC procedure for the monitoring of state dependent data, the CSPC procedure is applied to the following numerical example, which models a process of accumulated errors using a feedback control mechanism.

In many industrial processes, such as in chemical or metal welding processes, the process output is adjusted by applying a closed-loop controller to certain process variable(s). As an example, the temperature in a chemical reactor is controlled by a thermostat, or, the position of a robotic length of input sequences; v) the order of input symbols, etc. Further improvement of the model is possible by optimization of the manipulator is adjusted by a (PID) feedback controller. Such feedback controllers are likely to introduce dynamics and dependencies into the process output, which is affected by the accumulated adjustments and errors. It is, therefore, reasonable to try applying known SPC methods based on time-series to the monitored output. The question is whether traditional SPC methods can handle complex and state-dependent dynamics that might exist in the data. The example uses a simple mathematical model for a feedback-controlled system representative of the above and shows that traditional SPC methods fail to monitor the data whereas the CSPC performs well.

The example contains three parts: 1) derivation of the 'in-control' model for a feedback-controlled process by using the context algorithm; 2) application of CSPC to the monitored variables; and 3) comparison of the CSPC to Shewhart and other conventional time-series-based SPC methods.

1) Process Description and Derivation of 'In-Control' Model

The CSPC is applied to a feedback-controlled process, which is derived artificially, and follows the order-one Markov process represented by the state diagram shown in FIG. 12. The state diagram of FIG. 12 shows a series of numbered states 0, . . . ,4 and transitions therebetween, with probabilities associated with each transition. The process is based on a modified random-walk process restricted to a finite set of steps including zero.

The modified version of a random-walk process, as shown in FIG. 12 is generated as follows. First a realization sequence of N values is generated from an i.i.d Normal process, Norm (0,1), with mean $\mu_0=0$ and standard deviation $\sigma_0 1$. The sequence is inclusive of a representation of errors (white noise) added to the process output, whose mean is fixed on the target value. The underlying Normal distribution, Norm(0,1), permits a straightforward comparison to traditional SPC methods as seen below. Then, the string is quantized by selecting two thresholds to obtain a sequence of discrete steps $z_i \in \{-1,0,1\}, i=1,2,\ldots,N$. The cumulated sum of independent random steps thus defines an unconstrained random-walk process.

The values of the unconstrained random-walk are restricted to a constant symbol set using the modulo operation. In particular, the modulo(5) function is applied to the process data to obtain a symbol set of constant size d=5 of the values $\{0,1,2,3,4\}$. The restricted random-walk process models accumulated errors and follows the order-one Markov process presented in FIG. 12. Modelwise, the modulo operation can be viewed as a proportional feedback-control device, which is applied the output signal whenever the deviation is above a certain threshold.

Reference is now made to FIG. 13, which shows an analytical context-tree directly generated from the Markov diagram in FIG. 12. It is a single-level tree with S=5 contexts and a symbol set of d=5. A root node 70 displays the steady-state probabilities of the Markov process, and contexts 72.1 . . . 72.5 (the leaves) display the transition probabilities therein. The context-tree represents the 'in-control' reference distribution $P_0(x,s)$ of the process.

In the present, simplified, example, the context-tree model and the Markovian model are equivalent since the transition probabilities are known and the order of dependency is fixed. It is noted, however, that the context-tree model is more general than the Markovian since it allows modeling of processes that do not necessarily have a fixed order of dependency for different states. Moreover, the context algorithm enables an efficient estimation of such state dependent sources as discussed earlier.

Since the analytical model is often unknown in real-life situations, the convergence of the estimated context-tree, $\hat{P}_0(x,s)$, to the analytical context-tree $P_0(x,s)$ of FIG. 13 is now illustrated. Following the CSPC procedure, the context algorithm is applied to a data string generated using the restricted random-walk outlined above. As the string grows, any tree constructed from the string converges to the analytical model and the KL distance measure between them tends to zero, and reference is made to FIG. 14 which is a graph of KL value against string length. FIG. 14 shows the asymptotic convergence of the KL 'distance' between $\hat{P}_0(x,s)$ and $P_0(x,s)$ as a function of N—the string length.

The graph of FIG. 14 indicates that a longer input string results in an improved estimation of the analytical distributions $P_0(x,s)$. It also exhibits the rapid convergence of the context algorithm to the 'true' model. The dotted line indicates the weighted upper control limit of $\chi_{(24,0.9975)}^2/(2\cdot N)$ derived from equation 3.6 above. It is seen from FIG. 14 that for N>325, the KL value is constantly below the weighted UCL.

FIG. 14 may be used to assist an experimenter in determining the string length, N, required for a satisfactory estimation of the reference 'in-control' context-tree. In particular, for N<300 the KL measure is in transient mode, while for $300 \geq N \geq 700$ the KL measure stabilizes and then attains a steady state mode.

Reference is now made to FIG. 15, which shows an estimated reference context-tree obtained by an implementation of the context algorithm to N=1000 observations in the example. As with FIG. 12, the tree comprises a root node and leaves or contexts. A predictive approach is employed to compute the estimated conditional probabilities $\hat{P}_0(x|s), \forall x \in \chi, s \in T_N$.

As will be appreciated, the context algorithm performs well with respect to both the monitored tree structure and its estimated probability measures. Firstly, the context algorithm accurately identifies $\hat{P}_0(x,s)$ as a single-level tree containing S=5 optimal contexts that correspond to the Markov states. Secondly, the estimated conditional probabilities of symbols given contexts are relatively close to the analytical probabilities in terms of the KL statistics.

The structure of the reference context-tree is used to derive the UCL for the monitoring procedure. The UCL is calibrated to obtain a type I error probability of $\alpha=0.0025$, the type I error corresponding to the typical 3 sigma bound used in traditional SPC. Using equation 3.6, the UCL for the KL statistic is determined as $\chi_{(S \cdot d-1, 1-\alpha)}^2 = \chi_{(24,0.9975)}^2 = 48$.

2) CSPC Procedure: The Monitoring Stage

Two scenarios involving shifts of the underlying normal distribution, Norm(0,1), may be used to illustrate the performance of CSPC monitoring procedure, as follows:

i) Standard-deviation shifts: shifts in the standard deviation of the underlying normal process, denoted by $\sigma'=\lambda \cdot \sigma_0$, where $\sigma_0=1$; and $\lambda$ taking respectively the values of 1 ('in-control'), 0.5, 1.5 and 2; and ii) Mean shifts: shifts in the mean of like underlying normal process, denoted by $\mu'=\mu_0+\delta \cdot \sigma_0$, where $\mu_0=0$; $\sigma_0=1$; and $\delta$ varies between 0 to 3.

Different data streams are generated by the shifted Gaussian processes outlined in both scenarios. During the monitoring stage a fixed string length of N=125 data points is used to generate fifty monitored context-trees $\hat{P}_1(x,s) i=1,2,\ldots,50$ for each shifted process. Such a fixed string length preferably adheres to the chi-square sampling principle suggested by Cochram (1952) requiring that at least eighty percent of the sampling bins (corresponding in this case to the non-zero symbol counters of given optimal contexts n(x|s)) contain at least four data points.

Figure 17:
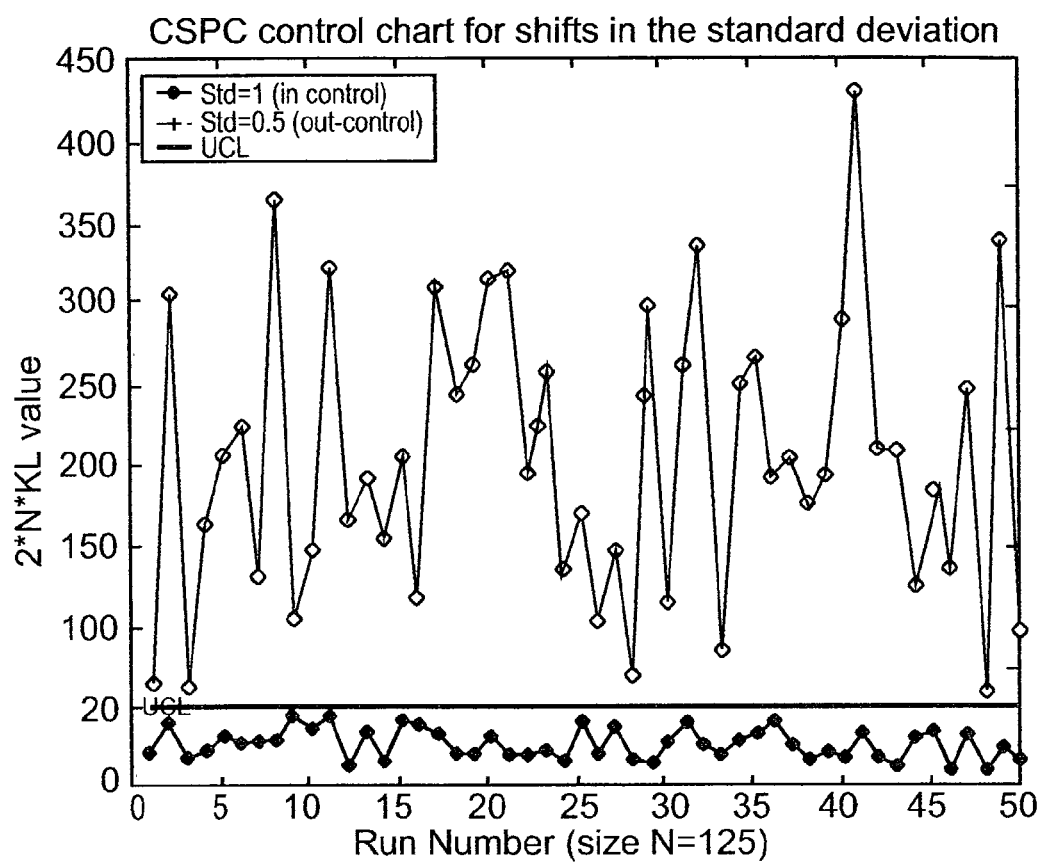

Scenario 1: Shifts in the Standard Deviation of the Underlying Normal Distribution The CSPC monitoring procedure, as outlined above, is applied herein to various standard deviation shifts of the underlying normal distribution. Fifty runs are generated from each shifted distribution with respective λ values of 1, 1.5, 2 and 0.5. Monitored trees are constructed for each run and the KL statistics between each monitored tree and the reference tree, are computed accordingly and plotted on the control chart. FIGS. 16 and 17 are control charts for all the shifted processes. Table 1 summarizes the results and presents both the probabilities of the random walk steps due to the shift in the underlying standard deviation and the corresponding Type II error.

TABLE 1 selection of processes to demonstrate CSPC

| Std Shift | Probability of the random-walk steps | | | Type 1 error | | ARL of S-chart benchmark) | |
|---|---|---|---|---|---|---|---|
| | | | | CSPC performance (ARL and Type 1 error) | | | |
| | | | | α | Estimate | ARL | ARL |
| λ | +1 | 0 | −1 | (No. of runs) | ARL | N = 5 | N = 125 |
| 1 | 0.16 | 0.68 | 0.16 | 100% (50) | ∞ | 333 | 250 |
| 1.5 | 0.25 | 0.5 | 0.25 | 80% (40) | 5 | 7.65 | 1 |
| 2 | 0.31 | 0.38 | 0.31 | 26% (13) | 1.35 | 2.35 | 1 |
| 0.5 | 0.02 | 0.976 | 0.02 | 0% (0) | 1 | ∞ | 1 |

As can he seen, for the 'in-control' process (λ=1), 100% of the runs are below the UCL, which implies that the type-I error probability of the CSPC procedure in the present example equals zero. For shifted processes, the rate of successful shift detection by the CSPC is relative to the transition probability change. Thus, for a standard deviation shift of λ=1.5 (resulting in a transition probability of 0.25 for each direction instead of 0.16), just 20% of the runs are above the UCL (FIG. 10, dotted line). However, for a standard deviation shift of λ=0.5 (resulting in a transition probability of 0.02 to each direction instead of 0.16), 100% of the runs are out of the control limits (FIG. 17). In comparison to many time-series-based SPC methods that are designed to detect shifts in process mean and, therefore, are not adequate for monitoring of shifts in the standard deviation, the CSPC is capable of identifying both type of shifts by using the same monitoring procedure (as exemplified in the next section). The reason is that shifts in the process mean and in the process standard deviation modify the transition probabilities, which in turn affect the KL statistic.

Scenario 2: Shifts in the Mean of the Underlying Normal Distribution

The CSPC performance in detecting mean shifts of the underlying normal distribution, $\mu'=\mu_0+\delta\cdot\sigma_0$, is presented by the Operating Characteristics (OC) curve. The OC curve plots the Type-II error ('in-control' probability) as a function of δ—the mean shift in the magnitude of the standard deviation.

Figure 18:
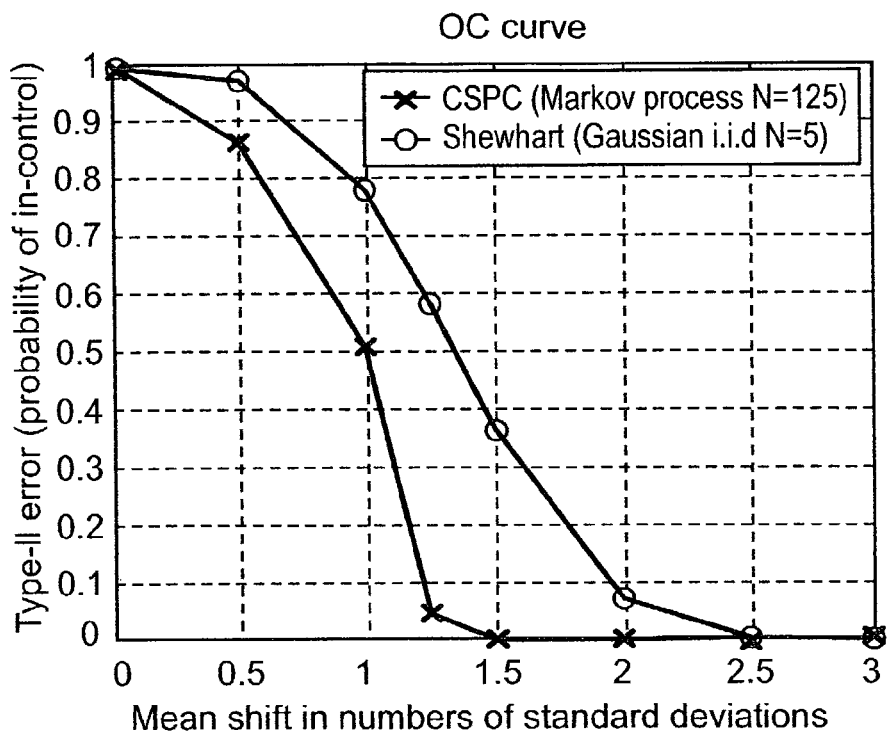

Reference is now made to FIG. 18, which is a simplified diagram showing the OC curve for the CSPC KL statistic of various runs, each run containing N=125 data points. The runs are generated from the modified random-walk process where the mean shift of the underlying Normal distribution varies between zero and three standard deviations ($\delta \in [0,3]$).

For reference purpose only, the OC curve for the traditional $\bar{\chi}$ statistic of an i.i.d Gaussian process with a sample size N=5 is also shown. It is true that such a difference in the sample sizes, as well as the fact that each statistic is applied here to a different process, makes a comparison between the two curves problematic, however, as will be shown below, when traditional SPC methods (Shewhart and time-series based) are applied to the same random-walk process, they are incapable of monitoring such state-dependent process, regardless of the sample size.

3) CSPC Procedure Comparison to Traditional Methods

Several studies (see, e.g., Box and Jenkins (1976) and Apley and Shi (1999)) have proposed to apply simple ARIMA models, such as AR(1) or IMA(1,1), to complex processes. These studies claim that simple ARIMA models require less estimation efforts and can successfully model a general autocorrelated process. Other studies (e.g., see Shore (2000)) have shown, in a similar manner, the capability and robustness of the Shewhart method in monitoring processes that deviate from the normality assumptions.

Herein, conventional SPC methods are applied to the random-walk process of FIG. 12. In general, all the conventional SPC methods that were tested failed to monitor the state-dependant process. In particular, the performance of Shewhart and ARIMA based approaches, that were suggested as 'general-purpose' monitoring, are focused on.

The first comparative prior art method used is an implementation of the Special Cause Chart (SCC) method suggested by Alwan and Roberts (1988) for autocorrelated data. The SCC monitors the residuals of ARIMA(p,d,q) filtering. The best-fit ARIMA model describing the random-walk process, as obtained by the Statgraphics software package, was the following AR(2) model: $\hat{x}_t=1.948+0.406\cdot x_{t-1}-0.0376\cdot x_{t-2}$, where $\epsilon_t=x_t-\hat{x}_{t-1}$.

Figure 19:
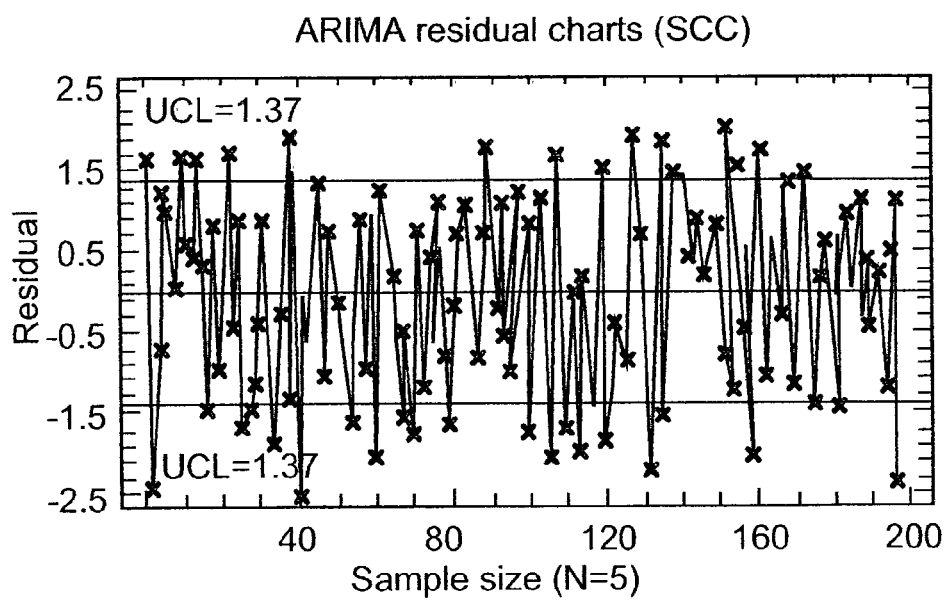

The residuals of the AR(2) filtering are accumulated in subgroups of size N=5 and charted by the Statgraphics software. For linear processes the residuals of the best-fit ARIMA filter are approximately uncorrelated and normally distributed. FIG. 19, which presents the SCC of the process output data, indicates that these assumptions are violated. A high number of false alarms, denoted by the star signs, renders the SCC uninformative. In particular, over 40% of data points in FIG. 19 are marked as 'out-of-control', although the random-walk process remained unchanged.

The ARIMA charts are thus shown to be inadequate to the task of modeling the above system. The ARIMA series fails to capture the state-dependant dynamics even in a simple order-one Markov model, resulting in violation of the independence and the normality assumptions of the residuals.

As a second comparative example, an implementation of the Shewhart method is used to monitor the random-walk process. Both the $\bar{\chi}$ chart to monitor the process mean, and the S chart to monitor the process standard deviation, are plotted. In order to evaluate the Shewhart performance, half of the runs are generated from the random-walk output data introduced above while the other half are generated from a random-walk which actually deviates from control limits. The latter process is generated by shifting the mean of the underlying normal distribution by one standard deviation, i.e., where $\mu'=\mu_0+1\cdot\sigma_0$.

Figure 20:
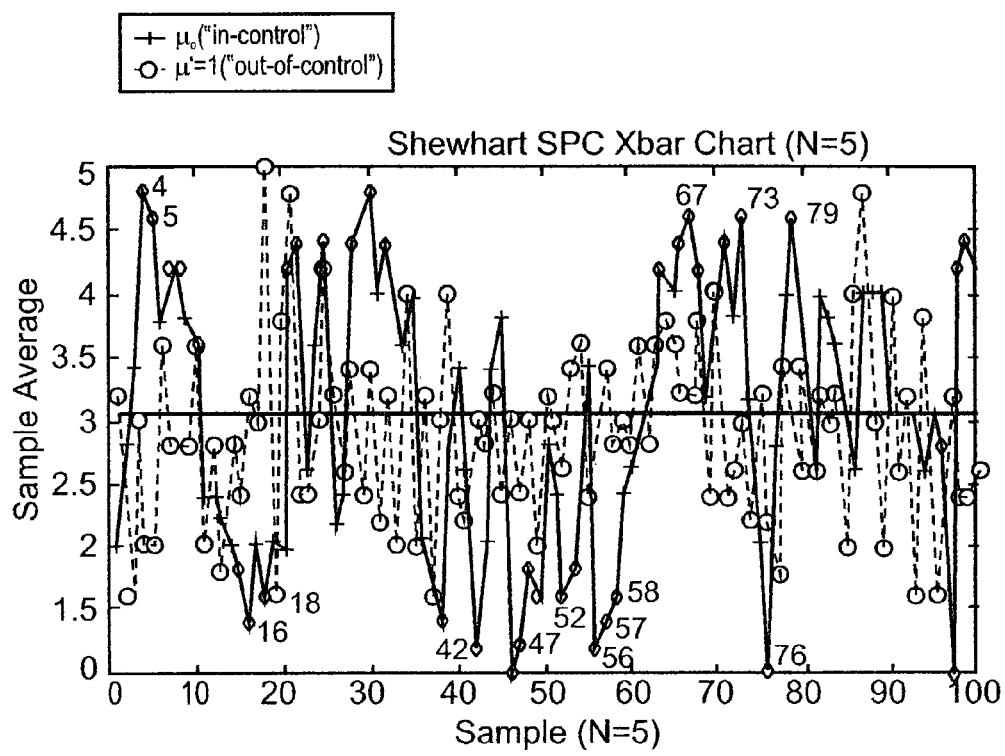
Figure 21:
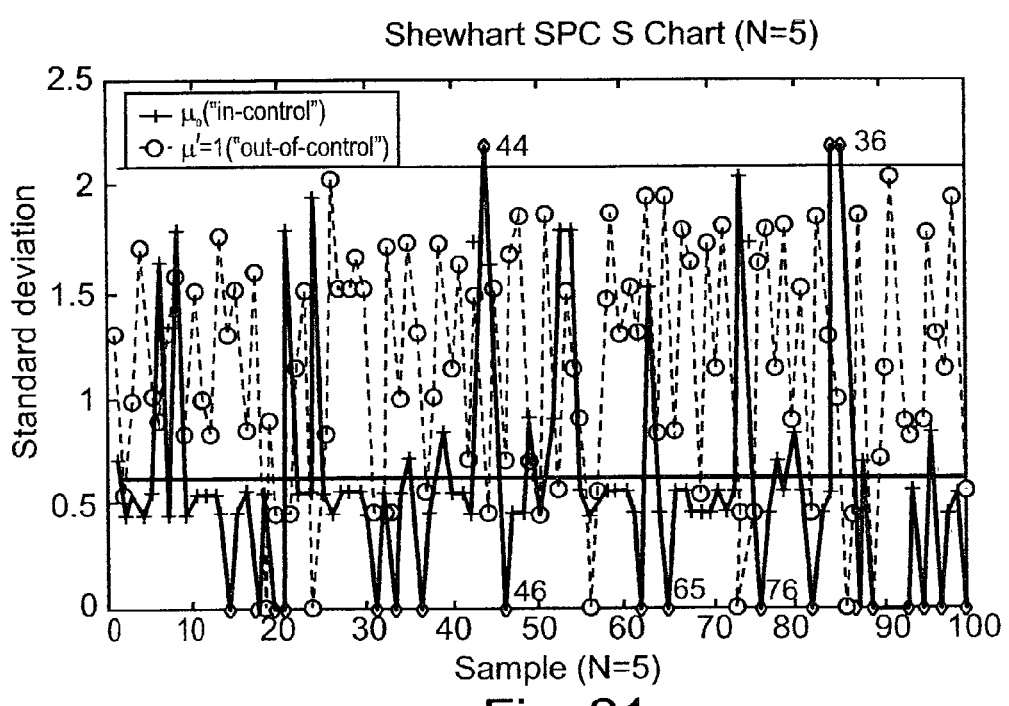

The $\bar{\chi}$ and S charts of both the 'in-control' data (solid line) and the 'out-of-control' data (dashed line) are presented, respectively, in FIGS. 20 and 21. The estimated parameters of the underlying distribution using a sample size N=5, are: $\hat{\mu}=\bar{\chi}=3.036$, and $\hat{\sigma}=\bar{S}=0.6148$, $\hat{\sigma}=\bar{S}/c_4=0.6148$, where $c_4$ is a correction constant to obtain an unbiased estimator for σ. It is pointed out that a high level appears for both statistical errors. The high type-I error is because the mean standard deviation of the naive Shewhart approach is relatively small. This is explained by the fact that neighbor observations in the random-walk tend to create a small sample variance (high probability for a step size of zero), but distant observations may have a larger standard deviation. The same phenomena are identified for shifts of two standard deviations' of the underlying process mean.

Figure 22:
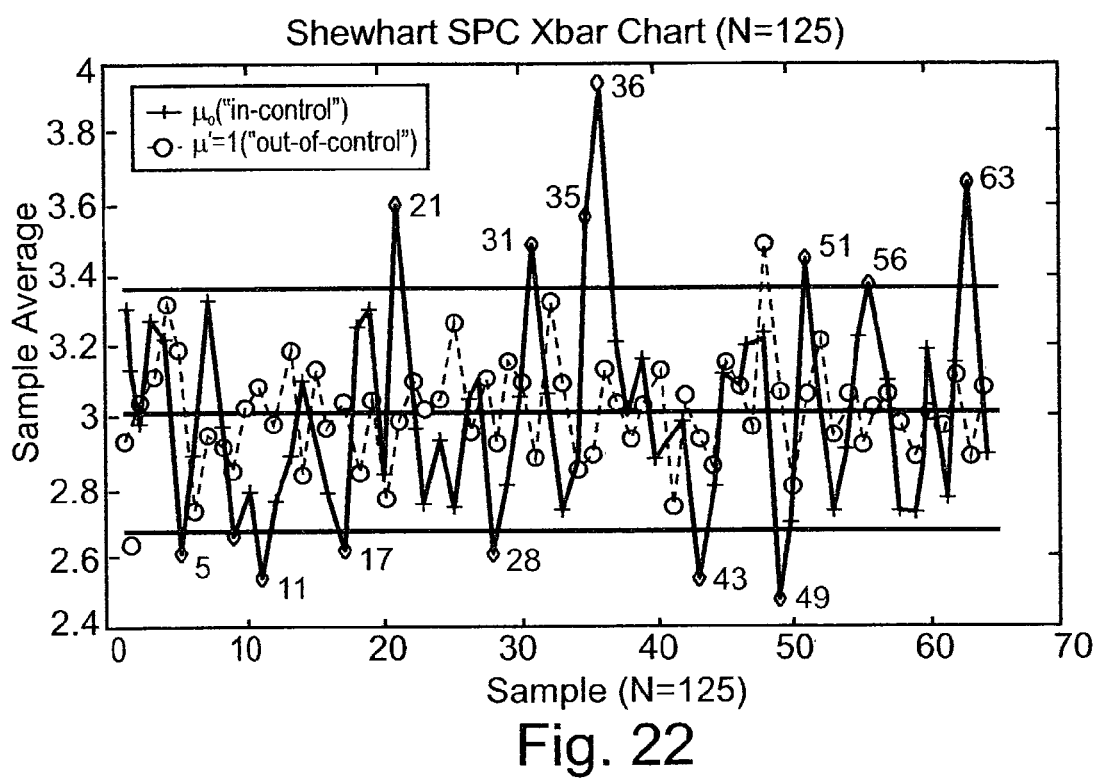
Figure 23:
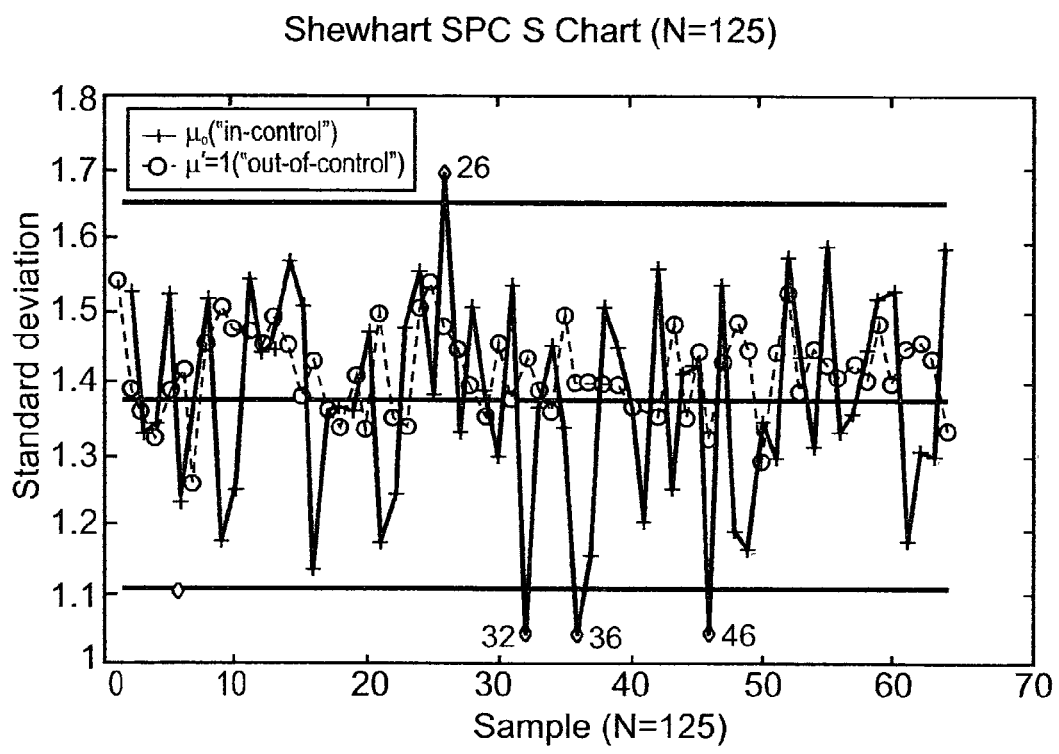

Reference is now made to FIGS. 22 and 23, which are Shewhart SPC $\bar{\chi}$ and S charts respectively for a repetition of the above experiment with a sample length of N=125, and showing in-control and out-of-control data.

The experiment was repeated in order to test whether increasing the value of the sample size N improves the performance of the Shewhart method, for example due to what is known in the art as the central limit theorem. In the repetition the sample size N was increased to N=125, which equals the sample size used by the CSPC in the specific embodiments to construct the context trees. The estimated parameters of the underlying distribution using a sample size N=125 are: $\hat{\mu}=\bar{\chi}=3.0129$, and $\hat{\sigma}=\bar{S}/c_4=1.3765$.

In the repetition, the estimated standard deviation doubled due to the increase in the size of the sample, which now contains data from different states of the process. Nevertheless a large number of samples generated by the 'in-control' random-walk are outside of the control limits. Paradoxically, the samples generated by the out-of-control random-walk appear steadier and more concentrated around a centrally drawn axis line in both charts. The reason is that an increase in the mean of the underlying distribution caused a constant intervention of the controller (modeled here by the modulo function), resulting in a decrease in the standard deviation of the modified random-walk.

The traditional Shewhart method can be successfully implemented to control processes that deviate from its underlying assumptions, but such implementations cannot be generalized to state-dependant processes. The Shewhart SPC is affective only when changes in the transition probabilities of a state-dependant process significantly affect the process mean. However, when this is not the case, the Markovian property violates the independence assumption, which assumption is in the core of the center limit theorem, and thus use of such a method in these circumstances results in unreliable control charts.

In general the Markov model does not take into account the possibility of position dependence in the model. The stochastic model discussed herein does take such position information into account.

APPLICATIONS

Use of the above context model to monitor changes in state has a wide range of applications. In general, the model part may be applied to any process which can be described by different arrangements of a finite group of symbols and wherein the relationship between the symbols can be given a statistical expression. The comparison stage as described above allows for changes in the statistics of the symbol relationships to be monitored and thus modeling plus comparison may be applicable to any such process in which dynamic changes in those statistics are meaningful.

A first application is statistical process control. A process produces a statistical output in terms of a sequence of symbols. As described above with respect to the numerical example, which illustrates control of a process involving feedback, the sequence can be monitored effectively by tree building and comparison.

Another SPC application is a serial production line having buffers in between in which a single part is manufactured in a series of operations at different tools operating at different speeds. The model may be used to express transitions in the levels at each of the buffers. The tree is constructed from a string built up from periodically observed buffer levels.

Stochastic models were built in the way described above in order to distinguish between coding and non-coding DNA regions. The models demonstrated substantial species independence, although more specific species dependent models may provide greater accuracy. Preliminary experiments concerned the construction of a coding model and a non-coding model each using 200 DNA strings divided into test sets and validation sets respectively.

Non-homogeneous trees that were applied to DNA segments of length 162 bp and a zero threshold, yielded a 94.8 percent of correct rejections (The negative) and 93 percent of correct acceptance (True Positive). Using another model with different threshold, we obtained a 99.5% of correct rejections for the coding model and a 21% of false rejections. Using the same model for the non-coding model, the percentage of correct rejections was 100% and the percentage of false rejections was 12%.

It was noted that the coding model had a much smaller context tree than the non-coding model.

Medical applications for the above embodiments are numerous. Any signal representing a body function can be discretized to provide a finite set of symbols. The symbols appear in sequences which can be modeled and changes in the sequence can be indicated by the comparison step referred to above. Thus medical personnel are provided with a system that can monitor a selected bodily function and which is able to provide an alert only when a change occurs. The method is believed to be more sensitive than existing monitoring methods.

A further application of the modeling and comparison process is image processing and comparison. A stochastic model of the kind described above can be built to describe an image, for example a medical image. The stochastic model may then be used to compare other images in the same way that it compares other data sequences. Such a system is useful in automatic screening of medical image data to identify features of interest. The system can be used to compare images of the same patient taken at different times, for example to monitor progress of a tumor, or it could be used to compare images taken from various patients with an exemplary image.

A further application of the modeling and comparison process is in pharmaceutical research. An enzyme carrying out a particular function is required. A series of enzymes which all carry out the required functions are sequenced and a model derived from all the sequences together may define the required structure.

A further application of the modeling and comparison process as described above is in forecasting. For example, such forecast can be applied to natural data—such as weather conditions, or to financial related data such as stock markets. As the model expresses a statistical distribution of the sequence, it is able to give a probability forecast for a next expected symbol given a particular received sequence.

A further application of the present embodiments is to sequences of multi-input single output data, such as records in a database, which may for example represent different features of a given symbol. Considering a database with records that arrive at consecutive times, the algorithm, (when extended to multi-dimensions), may compare a sequence of records and decide whether they have similar statistical properties to the previous records in the database. The comparison can be used to detect changes in the characteristics of the source which generates the records in the database.

Likewise the database may already be in place, in which case the algorithm may compare records at different locations in the database.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

The invention claimed is:

1. Apparatus embodied in a computer for building a stochastic model of a data sequence, said data sequence comprising time related symbols selected from a finite symbol set, the apparatus comprising:
   an input configured for receiving said data sequence, wherein said data sequence describes ongoing states of an observed process,
   a tree builder, configured for expressing said data sequence as a stochastic model, said stochastic model comprising said symbols as a series of counters within nodes, each node having a counter for each symbol, each node having a position within said tree, said position expressing a symbol sequence and each counter indicating a number of its corresponding symbol which follows a symbol sequence of its respective node,
   a tree reducer, configured for reducing said tree to an irreducible set of conditional probabilities of relationships between symbols in said input data sequence, and
   a comparator configured for comparing said reduced tree with a reference tree obtained in advance of said receiving sequential data so as to determine whether there has been a statistical change between said two trees, and for outputting a result of said comparing,
   wherein said data sequence is selected from a group consisting of: a manufacturing process output data sequence, a cyclic operating machine data sequence, a buffer level data sequence, a seismological data sequence, a medical sensor output data sequence, a sequence of financial data, a sequence of records arriving at a database, and an image data sequence.

2. Apparatus according to claim 1, said tree reducer comprising a tree pruner for removing from said tree any node whose counter values are within a threshold distance of counter values of a preceding node in said tree.

3. Apparatus according to claim 2, wherein said threshold distance and tree construction parameters are user selectable.

4. The apparatus of claim 3, wherein said user selectable parameters further comprise a tree maximum depth.

5. The apparatus of claim 3, wherein said user selectable parameters further comprise an algorithm buffer size.

6. The apparatus of claim 3, wherein said user selectable parameters further comprise values of pruning constants.

7. The apparatus of claim 3, wherein said user selectable parameters further comprise a length of input sequences.

8. The apparatus of claim 3 wherein, said user selectable parameters further comprise an order of input symbols.

9. Apparatus according to claim 2, wherein said tree reducer further comprises a path remover operable to remove any path within said tree that is a subset of another path within said tree.

10. Apparatus according to claim 1, wherein said sequential data is a string comprising consecutive symbols selected from a finite set.

11. The apparatus of claim 10, further comprising an input string permutation unit configured for carrying out permutations and reorganizations of the input string using external information about a process generating said string.

12. Apparatus according to claim 1, wherein said observed process comprises feedback.

13. Apparatus according to claim 1, wherein said data sequence comprises a seismological data sequence, and wherein said comparator is configured for providing said comparison result as a forecast of seismological activity.

14. Apparatus according to claim 1, wherein said data sequence comprises a medical sensor output data sequence, and wherein said apparatus is further configured for monitoring a selected bodily function.

15. Apparatus according to claim 14, wherein said medical sensor output data comprises visual image data and said medical sensor is a medical imaging device.

16. Apparatus embodied in a computer for determining statistical consistency in time sequential data, the apparatus comprising
   a sequence input configured for receiving sequential data, wherein said data sequence describes on going states of an observed process,
   a stochastic modeler configured for producing at least one stochastic model from at least part of said sequential data,
   and a comparator configured for comparing said sequential stochastic model with a reference model obtained in advance of said receiving sequential data so as to determine whether there has been a statistical change in said model, and for outputting a result of said comparing,
   wherein said data sequence is selected from a group consisting of: a manufacturing process output data sequence, a cyclic operating machine data sequence, a buffer level data sequence, a seismological data sequence, a medical sensor output data sequence, a sequence of financial data, a sequence of records arriving at a database, and an image data sequence.

17. Apparatus according to claim 16, wherein said stochastic modeler comprises:
   a tree builder configured for expressing symbols as a series of counters within nodes, each node having a counter for each symbol, each node having a position within said tree, said position expressing a symbol sequence and each counter indicating a number of its corresponding symbol which follows a symbol sequence of its respective node, and
   a tree reducer configured for reducing said tree to an irreducible set of conditional probabilities of relationships between symbols in said input data sequence.

18. Apparatus according to claim 16, said reference model being a model constructed using another part of said time-sequential data.

19. Apparatus according to claim 16, said comparator comprising a statistical processor configured for determining a statistical distance between said stochastic model and said reference model.

20. Apparatus according to claim 19, said statistical distance being a KL statistic.

21. Apparatus according to claim 19, said statistical distance being a relative complexity measure.

22. Apparatus according to claim 19, wherein said statistical distance comprises an SPRT statistic.

23. Apparatus according to claim 19, wherein said statistical distance comprises an MDL statistic.

24. Apparatus according to claim 19, wherein said statistical distance comprises a Multinomial goodness of fit statistic.

25. Apparatus according to claim 19, wherein said statistical distance comprises a Weinberger Statistic.

26. Apparatus according to claim 17, said tree reducer comprising a tree pruner configured for removing from said tree any node whose counter values are within a threshold distance of counter values of a preceding node in said tree.

27. Apparatus according to claim 26, wherein said threshold distance is user selectable.

28. The apparatus of claim 27, wherein user selectable parameters further comprise a tree maximum depth.

29. The apparatus of claim 27, wherein user selectable parameters further comprise an algorithm buffer size.

30. The apparatus of claim 27, wherein user selectable parameters further comprise values of pruning constants.

31. The apparatus of claim 27, wherein user selectable parameters further comprise a length of input sequences.

32. The apparatus of claim 27, wherein user selectable parameters further comprise an order of input symbols.

33. Apparatus according to claim 26, wherein said tree reducer further comprises a path remover operable to remove any path within said tree that is a subset of another path within said tree.

34. Apparatus according to claim 16, wherein said sequential data is a string comprising consecutive symbols selected from a finite set.

35. The apparatus of claim 34, further comprising an input string permutation unit configured for carrying out permutations and reorganizations of said sequential data using external information about a process generating said data.

36. Apparatus according to claim 16, wherein said observed process comprises feedback.

37. Apparatus according to claim 16, wherein said data sequence comprises a seismological data sequence, and wherein said comparator is configured for providing said comparison result as a forecast of seismological activity.

38. Apparatus according to claim 16, wherein said data sequence comprises output data sequences and wherein said apparatus is further configured for monitoring a selected bodily function.

39. Apparatus according to claim 19, wherein said data sequence comprises indications of a process state, the apparatus further comprising a process analyzer configured for using said statistical distance measure as an indication of behavior of said process.

40. Apparatus according to claim 19, wherein said data sequence comprises indications of a process state, the apparatus further comprising a process controller configured for using said statistical distance measure as an indication of behavior of said process, thereby to control said process.

41. Apparatus according to claim 20, wherein said data sequence comprises multi-input single output data.

42. Apparatus according to claim 16, wherein said data sequence comprises a sequence of financial data, and wherein said comparator is configured for providing said comparison result as a forecast of financial behavior.

43. Apparatus according to claim 16, wherein said data sequence comprises a time sequential image data sequences, and wherein said comparator is configured for providing said comparison result as an identification of features of interest in an image data.

44. Apparatus according to claim 43, said image data comprising medical imaging data, said statistical distance being indicative of deviations of said data from an expected norm.

45. Apparatus according to claim 16, wherein said data sequence comprises a sequence of records arriving at a database, and wherein said comparator is configured to perform data mining on said database.

46. A computer implementing a method for building a stochastic model of a data sequence, said data sequence comprising time related symbols selected from a finite symbol set, the method comprising:

receiving said data sequence, wherein said data sequence describes ongoing states of an observed process, expressing said symbols as a series of counters within nodes, each node having a counter for each symbol, each node having a position within said tree, said position expressing a symbol sequence and each counter indicating a number of its corresponding symbol which follows a symbol sequence of its respective node, reducing said tree to an irreducible set of conditional probabilities of relationships between symbols in said input data sequence, thereby to generate a stochastic model of said sequence, and comparing said stochastic model with a previously obtained reference model so as to determine if there has been a statistical change between the two models, and for outputting a result of said comparing, wherein said data sequence comprises one of a group consisting of: a manufacturing process output data sequence, a cyclic operating machine data sequence, a buffer level data sequence, a seismological data sequence, a medical sensor output data sequence, a sequence of financial data, a sequence of records arriving at a database, and an image data sequence.

47. The apparatus of claim 1, wherein said tree reducer is further configured to update said reference tree according to data in said reduced tree.

48. The apparatus of claim 1, wherein said trees represent non-homogeneous data.

49. The apparatus of claim 16, wherein said stochastic modeler is further configured to update said reference model according to data in said stochastic model.

50. The apparatus of claim 16, wherein said models represent non-homogeneous data.

51. The apparatus of claim 46, wherein said method further includes updating said reference model according to data in said stochastic model.

52. The method of claim 46, wherein said models represent non-homogeneous data.

53. Apparatus according to claim 1, further comprising an observation unit configured for generating said data sequence from measurements of one or more tangible objects.

54. Apparatus according to claim 16, further comprising an observation unit configured for generating said data sequence from measurements of one or more tangible objects.

55. Apparatus according to claim 1, wherein said method further comprises generating said data sequence from measurements of one or more tangible objects.

56. Apparatus according to claim 1, wherein said comparison result is provided as a control chart.

57. Apparatus according to claim 1, wherein said data sequence comprises a sequence of records arriving at a database, and wherein said comparator is configured for providing said comparison result as an identification of changes in a source generating said records.

58. Apparatus according to claim 1, wherein said data sequence comprises a sequence of records arriving at a database, and wherein said comparator is configured to perform data mining on said database.

* * * * *